United States Patent
Bayer et al.

(10) Patent No.: US 10,076,610 B2
(45) Date of Patent: Sep. 18, 2018

(54) DRIVE MECHANISM FOR A DRUG DELIVERY DEVICE

(71) Applicant: Sanofi, Paris (FR)

(72) Inventors: Stefan Bayer, Würselen (DE); Daniel Berning, Baesweiler (DE); Philippe Blank, Düsseldorf (DE); Wolfgang Pelzer, Kreuzau (DE); Michael Pfoser, Kohlscheid (DE); Björn Wilden, Simmerath (DE)

(73) Assignee: Sanofi, Paris (FR)

( * ) Notice: Subject to any disclaimer, the term of this patent is extended or adjusted under 35 U.S.C. 154(b) by 233 days.

(21) Appl. No.: 14/782,655

(22) PCT Filed: Apr. 8, 2014

(86) PCT No.: PCT/EP2014/056970
§ 371 (c)(1),
(2) Date: Oct. 6, 2015

(87) PCT Pub. No.: WO2014/166892
PCT Pub. Date: Oct. 16, 2014

(65) Prior Publication Data
US 2016/0067414 A1    Mar. 10, 2016

(30) Foreign Application Priority Data
Apr. 10, 2013    (EP) .................................... 13163069

(51) Int. Cl.
*A61M 5/315* (2006.01)
*A61M 5/20* (2006.01)

(52) U.S. Cl.
CPC .......... *A61M 5/31541* (2013.01); *A61M 5/20* (2013.01); *A61M 5/3157* (2013.01);
(Continued)

(58) Field of Classification Search
CPC .................. A61M 2005/3154; A61M 5/31541
See application file for complete search history.

(56) References Cited

U.S. PATENT DOCUMENTS

2006/0153693 A1    7/2006  Fiechter et al.
2008/0306445 A1   12/2008  Burren et al.
(Continued)

FOREIGN PATENT DOCUMENTS

JP    2009-502273    1/2009
JP    2011-519600    7/2011
(Continued)

OTHER PUBLICATIONS

International Preliminary Report on Patentability in International Application No. PCT/EP2014/056970, dated Oct. 13, 2015, 7 pages.
(Continued)

*Primary Examiner* — Andrew Gilbert
*Assistant Examiner* — John Doubrava
(74) *Attorney, Agent, or Firm* — Fish & Richardson P.C.

(57) ABSTRACT

A drive mechanism for a drug delivery device includes an elongated housing extending in an axial direction and a piston rod to operably engage with a piston of a cartridge to displace the piston in an axial distal direction. A drive sleeve is rotatably supported in the housing, operably releasable from the piston rod for setting of a dose, and operably engageable with the piston rod for dispensing of the dose. A dose limiting member is engaged with the drive sleeve and engaged with the piston rod in such a way that it is displaced in axial direction relative to the drive sleeve when the drive sleeve rotates relative to the piston rod during a dose setting procedure. At least one stop is configured to engage with the dose limiting member for limiting the axial displacement of
(Continued)

the dose limiting member during the dose setting procedure and to impede further displacement of the drive sleeve relative to the piston rod.

22 Claims, 16 Drawing Sheets

(52) U.S. Cl.
CPC .... *A61M 5/31553* (2013.01); *A61M 5/31583* (2013.01); *A61M 2005/3154* (2013.01); *A61M 2205/581* (2013.01); *A61M 2205/582* (2013.01)

(56) References Cited

U.S. PATENT DOCUMENTS

| | | |
|---|---|---|
| 2011/0054412 A1 | 3/2011 | Eich et al. |
| 2012/0245532 A1* | 9/2012 | Frantz ............... A61M 5/31551 604/211 |

FOREIGN PATENT DOCUMENTS

| | | |
|---|---|---|
| WO | WO 2004/078239 | 9/2004 |
| WO | WO 2006/069456 | 7/2006 |
| WO | WO 2006/079481 | 8/2006 |
| WO | WO 2007/017052 | 2/2007 |
| WO | WO 2009/132778 | 11/2009 |
| WO | WO 2013/010884 | 1/2013 |

OTHER PUBLICATIONS

International Search Report and Written Opinion in International Application No/PCT/EP2014/056970, dated Jul. 23, 2013, 12 pages.

* cited by examiner

A-A

B-B

C-C

D-D

E-E

F-F

DRIVE MECHANISM FOR A DRUG DELIVERY DEVICE

CROSS-REFERENCE TO RELATED APPLICATIONS

This application is a U.S. national stage application under 35 USC § 371 of International Application No. PCT/EP2014/056970, filed on Apr. 8, 2014, which claims priority to European Patent Application No. 13163069.1, filed on Apr. 10, 2013, the entire contents of which are incorporated herein by reference.

The present invention relates to a drive mechanism for a drug delivery device and to a respective drug delivery device. In particular, the invention relates to an injection device such like a pen-type injector comprising a single and/or a last-dose limiting mechanism.

BACKGROUND AND PRIOR ART

Drug delivery devices for setting and dispensing a single or multiple doses of a liquid medicament are as such well-known in the art. Generally, such devices have substantially a similar purpose as that of an ordinary syringe.

Drug delivery devices, in particular pen-type injectors have to meet a number of user-specific requirements. For instance, with patient's suffering chronic diseases, such like diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Moreover, a dose setting as well as a dose dispensing procedure must be easy to operate and has to be unambiguous.

Typically, such devices comprise a housing, adapted to receive a cartridge at least partially filled with the medicament to be dispensed. The device further comprises a drive mechanism, typically having a displaceable piston rod which is adapted to operably engage with a piston of the cartridge. By means of the drive mechanism and its piston rod, the piston of the cartridge is displaceable in a distal or dispensing direction and may therefore expel a predefined amount of the medicament via a piercing assembly, which is to be releasably coupled with a distal end section of the housing of the drug delivery device.

The medicament to be dispensed by the drug delivery device is provided and contained in a multi-dose cartridge. Such cartridges typically comprise a vitreous barrel sealed in distal direction by means of a pierceable seal and being further sealed in proximal direction by the piston. With reusable drug delivery devices an empty cartridge can be replaced by a new one. In contrast to that, drug delivery devices of disposable type are to be entirely discarded when the medicament in the cartridge has been dispensed or used-up.

With such multi-dose drug delivery devices at least a last dose limiting mechanism is required to inhibit setting of a dose exceeding the amount of medicament which is left in the cartridge. This is to avoid a potentially dangerous situation for the user believing that a set dose is entirely injected.

There already exist some drug delivery devices with such end-of-content mechanisms or last dose mechanisms.

Document WO 2009/132778 A1 for instance discloses a dose limiting member designed for axial movement in a proximal direction with respect to the piston rod during dose setting. The dose limiting member comprises a first stop element and the piston rod comprises a second stop element. First and second stop elements stop an axial movement of the dose limiting member in the proximal direction with respect to the piston rod when the first and second stop elements catch, thereby limiting a movement of the dose setting member for increasing a set dose of medication to be delivered. There, the dose limiting member and the piston rod only interact directly, when the first and second stop elements catch.

Apart from such a last dose limiting mechanism it may be also required to provide a single dose limiting mechanism by way of which the maximum size of a dose to be set and dispensed can be limited to a predefined maximum.

It is therefore an object of the present invention to avoid disadvantages of known drug delivery devices and to provide a single dose limiting mechanism as well as a last dose limiting mechanism.

It is another object of the present invention to provide a drive mechanism for a drug delivery device for setting and dispensing of a dose of a medicament typically provided in a cartridge, wherein the drive mechanism is equipped with a single dose limiting mechanism and with a last dose limiting mechanism.

It is a further object to provide a drug delivery device comprising such a drive mechanism and comprising a cartridge sealed with a piston to become operably engaged with a piston rod of such drive mechanism.

In a first aspect a drive mechanism for a drug delivery device is provided for dispensing of a dose of a medicament. The drive mechanism comprises an elongated housing extending in an axial direction. Preferably, the housing is of substantially tubular or cylindrical shape that allows gripping and operating of the drive mechanism or of the entire drug delivery device by one hand of a user.

The drive mechanism further comprises a piston rod to operably engage with a piston of a cartridge containing the medicament to be dispensed by the drive mechanism. The cartridge comprises a piston, which, by means of a displacement in axial distal direction, serves to expel an amount of the medicament from the cartridge that corresponds to the axial displacement of the piston. The piston typically seals the cartridge in axial proximal direction. The piston rod serves to displace the piston of the cartridge in an axial distal direction. The piston rod is therefore operable to apply distally directed thrust or pressure to the piston of the cartridge for displacing the same in distal direction for a predetermined distance that corresponds to a respective amount of the medicament to be dispensed.

The drive mechanism further comprises at least one drive sleeve which is rotatably supported in the housing and which is operably releasable from the piston rod for setting of a dose. Hence, during a dose setting procedure, the piston rod remains substantially stationary with respect to the housing while the drive sleeve, operably disconnected and released from the piston rod, is rotatable relative to the housing and hence relative to the piston rod.

However, for dispensing of the set dose, the drive sleeve is operably engageable with the piston rod. In a respective dose dispensing mode, piston rod and drive sleeve are operably engaged for that the drive sleeve may exert a driving force or driving momentum to the piston rod for driving the same in distal direction to displace the piston of the cartridge accordingly.

The drive mechanism further comprises a dose limiting member engaged with the drive sleeve and engaged with the piston rod in such a way, that the dose limiting member is displaced in axial direction relative to the drive sleeve and/or relative to to the piston rod when the drive sleeve rotates relative to the piston rod during a dose setting procedure. The dose limiting member is provided as a separate component of the drive mechanism and is directly engaged with the drive sleeve as well as with the piston rod.

The drive mechanism further comprises at least one stop for limiting the axial displacement of the dose limiting member during the dose setting procedure. The at least one stop typically comprises a stop face to engage or to abut with the dose limiting member when a dose limiting configuration of the drive mechanism has been reached during a dose setting procedure. When the at least one stop and the dose limiting member mutually engage, the at least one stop serves to impede or to block further displacement of the drive sleeve relative to the piston rod.

Since the dose limiting member is directly engaged with both, the drive sleeve and with the piston rod, the mutual engagement of the at least one stop with the dose limiting member also serves to impede a further displacement of the drive sleeve relative to the housing. By impeding or blocking the displacement of the drive sleeve relative to the piston rod and/or relative to the housing, a dose setting procedure can be interrupted and blocked.

By means of the separate dose limiting member a single dose limiting mechanism can be implemented allowing to limit or to confine the maximum amount of the medicament of a single dose during a dose setting procedure. The maximum size of a dose is correlated to the mutual engagement of the dose limiting member with the drive sleeve and/or with the piston rod. Moreover, the size of the maximum dose to be limited by the single dose limiting mechanism can be further varied and specified by the geometry of the dose limiting member as well as by the geometry, position and orientation of the at least one stop.

Moreover, interchanging of the dose limiting member by a dose limiting member of different size or geometry allows to modify the size of the maximum dose to be set and to be dispensed by the drive mechanism and by the respective drug delivery device. In this way, the drive mechanism can be in principle adapted and configured to different medication requirements. In case of e.g. a drug delivery device for injecting insulin from a cartridge, the dose limiting member may be configured to set a maximum dose of 120 international units (I.U.). For other drug delivery devices or for a different medicament or medicament type, a maximum dose of e.g. 80 I.U. or 50 I.U. may be required.

Variable sizes of maximum doses may be easily implemented with the drive mechanism by replacing the dose limiting member with a differently configured dose limiting member. For instance, respective dose limiting members may differ with regard to their axial extension and size.

In a further embodiment, the drive sleeve encloses the circumference of the piston rod at least in an axial section. Typically, the drive sleeve is open towards the distal direction and receives or accommodates a proximal portion of the piston rod, at least in an initial device configuration. The piston rod and the surrounding drive sleeve are typically arranged concentrically. Hence, the piston rod is located in the radial centre of the drive sleeve and is co-aligned with the drive sleeve in axial direction. While the drive sleeve is rotatably supported in the housing it may only experience a limited axial displacement, e.g. for switching between a dose setting mode and a dose dispensing mode of the drive mechanism. In contrast to that, the piston rod advances in distal direction with every consecutive dose dispensing procedure. With repeated dose dispensing procedures the piston rod may therefore protrude more and more in axial direction from the drive sleeve.

The dose limiting member is further arranged radially between the drive sleeve and the piston rod. Due to the location between the drive sleeve and the piston rod, the dose limiting member is engaged with an inside facing surface of the drive sleeve and with an outside facing surface of the piston rod. By arranging the dose limiting member radially between the drive sleeve and the piston rod, the single dose limiting mechanism can be provided substantially inside the drive sleeve, which allows for a rather space-saving arrangement of the single dose limiting mechanism. In this way, the outer circumference of the drive sleeve does not have to provide any means for a single dose limiting mechanism. As a consequence, the drive sleeve can be designed in a rather compact way.

According to a further embodiment, the dose limiting member is threadedly engaged with the drive sleeve. For this purpose, the dose limiting member comprises an outer thread to engage with a correspondingly designed inner thread of the drive sleeve. By means of the threaded engagement of dose limiting member and drive sleeve, a rotation of the drive sleeve relative to the piston rod can be transferred to an axial displacement of the dose limiting member, given that the dose limiting member is hindered to rotate with the drive sleeve.

In a further preferred embodiment, the dose limiting member is rotatably fixed to the piston rod but it is axially slideably engaged with the piston rod. In other words the dose limiting member is splined to the piston rod. Hence, the dose limiting member cannot rotate relative to the piston rod but is free to slide along the piston rod in axial direction. Since the dose limiting member is axially slideably engaged with the piston rod it may slide along the piston rod in axial direction during a relative rotation of drive sleeve and piston rod.

Preferably, the dose limiting member is displaceable in proximal direction during a dose setting procedure and is operable to return to an initial position in distal direction during a dose dispensing procedure.

Since the dose limiting member is splined to the piston rod and since the dose limiting member is threadedly engaged with the drive sleeve, it is engaged with the drive sleeve and with the piston rod in such a way, that it is displaced in axial direction relative to the drive sleeve when the drive sleeve rotates relative to the piston rod during a dose setting procedure.

According to an alternative embodiment it is also conceivable that the dose limiting member is rotatably fixed to the drive sleeve but is axially slideably engaged with the drive sleeve. At the same time, the dose limiting member is threadedly engaged with the piston rod. Also in this configuration, the dose limiting member is engaged with the drive sleeve and with the piston rod in such a way, that it is displaced in axial direction relative to the drive sleeve when the drive sleeve rotates relative to the piston rod during a dose setting procedure.

In this alternative embodiment, the dose limiting member is splined with the drive sleeve and is therefore rotatably coupled with the drive sleeve. A rotation of the drive sleeve is therefore unalteredly transferable to a respective rotation of the dose limiting member. Due to the threaded engagement of the dose limiting member and the piston rod, the dose limiting member may preferably displace relative the piston rod in proximal direction during a dose setting procedure initiated by the drive sleeve.

The alternative embodiment, wherein the dose limiting member is splined with the drive sleeve and wherein the dose limiting member is threadedly engaged with the piston rod provides an alternative approach of a mutual engagement of dose limiting member, drive sleeve and piston rod for displacing the dose limiting member relative to the drive sleeve and/or relative to the piston rod in axial, preferably in proximal direction during a dose setting procedure.

In another embodiment, wherein the dose limiting member is threadedly engaged with the drive sleeve and wherein the dose limiting member is rotatably fixed to the piston rod, the piston rod comprises an axially elongated groove or notch to receive a radially inwardly extending gliding portion of the dose limiting member. The gliding portion of the dose limiting member provides a kind of a tappet mating and engaging with the geometry of the piston rod's groove. The gliding portion therefore serves to rotatably fix the dose limiting member to the piston rod. Moreover, it provides a controlled axially directed sliding displacement of the dose limiting member relative to the piston rod.

Preferably, the piston rod comprises an outer thread to engage with the housing or with another component of the drive mechanism, e.g. a drive nut of the drive mechanism. In such embodiments, the elongated groove of the piston rod intersects and interrupts the external thread of the piston rod.

Moreover, by the elongated groove, the piston rod can be in principle splined to the housing of the drive mechanism and/or of the drug delivery device. In this way, the axially elongated groove of the piston rod provides a double function. When arranged in the housing of the drive mechanism, the groove may engage with at least one radially inwardly extending protrusion of the housing of the drive mechanism and/or of the drug delivery device, thereby preventing a rotational movement of the piston rod relative to the housing. Moreover, the same axially elongated groove may provide a longitudinal, hence axial guiding structure for the dose limiting member for rotatably fixing the dose limiting member to the piston rod and hence to the housing.

According to another embodiment, the dose limiting member comprises a shell-like profile, in particular a half-shell profile, extending only partially around the circumference of the piston rod. Preferably, the dose limiting member comprises a substantially even shaped inner surface, which allows the dose limiting member to glide over the threaded piston rod in axial direction. Alternative to a shell profile, the dose limiting member may also be designed as a dose limiting sleeve completely extending around the outer circumference of the piston rod. However, for the purpose of limiting relative displacement of drive sleeve and piston rod, a shell-like profile of the dose limiting member may already be sufficient. A shell-like or half-shell profiled dose limiting member may be beneficial in terms of assembly of the drive mechanism and may further provide to reduce material costs and overall weight of the drive mechanism.

According to another embodiment, the at least one stop extends in radial direction and in axial direction to engage with a correspondingly oriented stop portion of the dose limiting member. This way, a so-called radial stop can be implemented, by way of which a rotational displacement of the stop portion of the dose limiting member relative to the at least one stop can be interrupted and blocked. Moreover, since the stop and the correspondingly oriented stop portion extend in radial direction and in axial direction, respective stop faces can be provided, which when partially overlapping in axial direction, may also allow for relative axial displacement of the dose limiting member with respect to the stop.

According to another preferred embodiment, the dose limiting member comprises a distal stop portion and a proximal stop portion extending from opposite distal and proximal end sections thereof. By having a distal stop portion extending from a distal end of the dose limiting member, the drive mechanism can be effectively locked in a zero dose configuration, which is typically reached at the end of a dose dispensing procedure. The proximal stop portion which extends from the opposite proximal end section of the dose limiting member is adapted to lock the drive mechanism in a maximum dose configuration for limiting the size of a maximum single dose to be set and to be subsequently dispensed by the drive mechanism. At least one of the stop portions of the dose limiting member, preferably both stop portions, extend within tangential circumference of the dose limiting member. Preferably, the at least one stop portion does not radially protrude from the circumference of the dose limiting member.

Distal and proximal stop portions of the dose limiting member are particularly adapted to separately engage or to separately interact with respective distal and proximal stops of the drive mechanism, for limiting a rotational displacement of the drive sleeve during dose setting as well as during a subsequent dose dispensing procedure. Here, the dose limiting member provides a double function. It serves to confine and to delimit the dose setting procedure as well as the dose dispensing procedure. In particular, the distal and the proximal stop portions of the dose limiting member and their corresponding stops are arranged and oriented in such a way, that engagement of a proximal stop portion of the dose limiting member with a respective proximal stop defines a zero dose configuration, wherein the size of the dose equals zero. Moreover, the mutual engagement of the distal stop portion of the dose limiting member with a corresponding distal stop specifies and defines a maximum dose configuration or a single dose limiting configuration.

According to a further embodiment, the at least one stop is arranged at an inside wall of the drive sleeve. In this embodiment, the at least one stop preferably serves as a distal stop to engage with the distal stop portion of the dose limiting member. The distal stop of the drive sleeve preferably extends in axial and radial direction and therefore provides a stop face to engage with the correspondingly oriented distal stop portion of the dose limiting member. The at least one stop of the drive sleeve may radially inwardly protrude from the drive sleeve in order to engage with the distal stop portion of the dose limiting member. When getting in a mutual engagement configuration or in a mutual radial abutment, the drive sleeve is preferably in a zero dose configuration, i.e. at the end of a dose dispending procedure.

Generally, a radially and axially extending stop provides an accurate, well-defined and reproducable stop configuration for those components featuring such mutually engaging stop features. A radial stop generally provides a radially outwardly and/or radially inwardly extending structure provided at a particular tangential position on the inner and/or outer circumference of e.g. a tubular shaped component. In this way, a definite and well defined stop configuration can be provided which is much more precise and less sensitive to an eventual self-locking which may otherwise occur with an axial stop, such like a radially extending flange extending at a particular axial position of e.g. a last dose sleeve.

However, in alternative embodiments implementation of such axial stops is also generally conceivable, also in combination with radially acting stops.

According to a further embodiment, the at least one stop is arranged on and axially protrudes from a distal end of a clutch operably engaged with the drive sleeve. This stop provided on the clutch serves as a proximal stop to engage with the proximal stop portion of the dose limiting member. The at least one stop provided on the clutch preferably extends in distal direction from the distal end thereof. The clutch is typically located axially offset from the drive sleeve in proximal direction.

The drive sleeve is preferably subject to a rotational displacement during a dose setting procedure and may be operably engaged with the clutch. It is of particular benefit here, that its distal end and the correspondingly configured distal stop portion of the dose limiting member both comprise mutually abutting stop faces that extend in radial and axial direction.

Generally, the proximal stop typically provided on the distal end of the clutch could also be arranged at an inside wall of the drive sleeve and could extend radially inwardly from said wall to radially engage with the proximal stop portion of the dose limiting member when reaching the dose limiting or maximum dose configuration of the drive mechanism.

According to a further embodiment, the dose limiting member comprises a clicking member at a distal end having a resilient arm extending in circumferential or tangential direction. The resilient arm further comprises a latch or nose portion at a free end thereof to audibly engage with the stop, in particular with the distal stop before or when the stop portion, in particular the distal stop portion, engages with the stop. The clicking member extends in circumferential direction from the stop portion of the dose limiting member so that the clicking member reaches the stop prior to the stop portion during a rotation of the drive sleeve. The clicking member therefore advances the respective stop portion of the dose limiting member upon rotation of the drive sleeve. Preferably, the clicking member is provided at the distal end of the dose limiting member. It may therefore advance the distal stop portion of the dose limiting member.

The resilient arm of the clicking member allows for a resilient axial displacement of the clicking member when e.g. passing the distal stop provided on the inside wall of the drive sleeve. The nose or latch portion of the clicking member is designed such, that the clicking member passes the stop of the drive sleeve while the arm resiliently deforms. After the clicking member and in particular its latch portion has completely traversed the stop of the drive sleeve, the biased resilient arm will return into its initial unbiased configuration and may thus generate an audible click sound. Since the clicking member advances the motion of the trailing distal stop portion of the dose limiting member, the click sound generated by the clicking member is directly indicative that the end of a dose injection procedure approaches or that the end of the dose injection procedure has just been reached.

The clicking member is preferably provided at the distal stop portion of the dose limiting member. However, it may be correspondingly provided also at a proximal stop portion of the dose limiting member, thereby audibly indicating that the maximum dose configuration is reached or is almost reached in a dose setting procedure.

According to another preferred embodiment, the stop extends radially in or on the piston rod to engage with the dose limiting member in a last dose configuration of the drive mechanism. When interacting with the dose limiting member said stop provides a last dose limiting mechanism or an end-of-content mechanism. Since the axial position of the piston rod is unequivocally correlated to the axial position of the piston in the cartridge, the position of the piston rod is directly indicative of the filling level of the cartridge.

The stop provided in or on the piston rod typically extends in radial direction. It may extend radially inwardly, e.g. to engage with a radially inwardly extending gliding portion or tappet of the dose limiting member. It may also extend radially outwardly from the circumference or from the bottom of the groove of the piston rod. By providing a radially extending stop in or on the piston rod, axial displacement of the dose limiting member during a dose setting procedure can be appropriately limited, in such situations, where the medicament left in the cartridge is less than a dose a user is intending to set and to dispense.

Mutual engagement of the dose limiting member with the radially outwardly extending stop of the piston rod hinders the dose limiting member to be displaced further in proximal direction during a dose setting procedure. In this way and due to the mutual engagement of the dose limiting member with the piston rod and with the drive sleeve, a further rotation of the drive sleeve to increase a dose is effectively inhibited so that setting of a dose that would otherwise exceed a remaining filling level of the cartridge cannot take place.

In this embodiment, the stop extending radially in or on the piston rod serves as a last dose stop. It may but does not have to extent from a proximal end of the piston rod and may comprise a flange-like geometry.

In configurations wherein the dose limiting member slides along an axial groove of the piston rod, the last dose stop of the piston rod may be implemented in form of a proximal end of the groove. Here, the last dose stop may confine the groove in proximal direction and may provide a radially inwardly extending stop face, by means of which a proximally directed displacement of the dose limiting member can be restricted accordingly.

Hence, the last dose stop provided on or in the piston rod is adapted and designed to axially abut with a correspondingly shaped proximal stop portion of the dose limiting member.

According to this embodiment, the dose limiting member fulfils a double function. On the one hand, the dose limiting member may serve to implement a single dose limiting means, e.g. in that its proximal stop portion engages with a proximal stop arranged on a distal end of a clutch. On the other hand, the dose limiting member with its proximal stop portion may also provide a last dose limiting mechanism when the proximal stop portion engages with a last dose stop in or on the piston rod.

According to another embodiment, the drive sleeve is rotatably biased relative to the housing by means of a helical spring extending around the drive sleeve. By having arranged the dose limiting member inside the drive sleeve it does not hinder a nested arrangement of the drive sleeve in a helical spring extending there around. The helical spring is coupled with one end with the drive sleeve while another end of the helical spring is preferably coupled and connected with the housing. This way, the drive sleeve is rotatably supported for setting of a dose relative to housing against the action of the helical spring.

Such rotational and spring biasing displacement of the drive sleeve is preferably accompanied and controlled by a ratchet mechanism having at least one ratchet member to engage with a toothed surface of the housing to prevent uncontrolled and counter-directed rotation of the drive sleeve. Typically, the drive sleeve may comprise a resiliently deformable arc-shaped ratchet member extending along the outer circumference of the drive sleeve and having a ratchet tooth or nose extending radially outwardly and mating with a correspondingly shaped toothed surface provided on the inner wall of the housing. This way, the drive sleeve may be rotated in a dose setting direction in an incremented way as governed by the size of the toothed surface. Moreover, a dose incrementing dial or rotation of the drive sleeve is accompanied with an audible click-sound generated by the ratchet member meshing with the toothed surface.

Mutual engagement of the ratchet member of the drive sleeve with the toothed surface of the housing is further designed in such a way, that a user may also correct the size of a set dose, e.g. by rotating the drive sleeve in an opposite direction. However, for such a correcting and oppositely directed rotation of the drive sleeve, application of a counter-directed correction force is to be applied, which is larger than a holding force provided by the mutual engaging ratchet member and the toothed surface.

Apart from application of a counter-directed correction force above a predefined force level, other dose-correcting mechanisms are also conceivable here by means of which the ratchet mechanism may be temporally overridden.

According to a further embodiment, the piston rod is threadedly engaged with a drive nut which is axially fixed to the housing and which is rotatably supported in the housing. Preferably, drive nut and drive sleeve are co-aligned around the piston rod. The drive nut may be located distally from a distal end of the drive sleeve and it is preferably axially secured in the housing. The piston rod is typically splined to the housing or with an insert positioned in the housing and providing a radially inwardly extending flange or web with a through opening, through which the piston rod may extent axially.

It is to be mentioned here, that the insert is fixed and immobilized to the housing. The insert may be provided as a separate component to be assembled in the housing. Alternatively, insert and housing may be integrally formed. Hence, any reference made herein to the housing is equivalently valid for the housing and vice versa.

The through opening of the flange or web of the housing or of the respective insert comprises at least one radially inwardly extending protrusion that mates and engages with the at least one axially elongated groove of the piston rod. Consequently, the piston rod is rotatably fixed to the housing and is effectively hindered to rotate relative to the housing. A distally directed displacement of the piston rod relative to the housing can thus be attained by the rotating drive sleeve threadedly engaged with the piston rod.

The drive sleeve is preferably only free to rotate in one direction relative to the housing that corresponds to a dose setting procedure, during which the piston rod is driven in distal direction. Hence, the drive sleeve may be equipped with another ratchet mechanism operating in an opposite sense compared to the ratchet mechanism of the drive sleeve. The drive sleeve's ratchet mechanism only allows a dispensing-correlated rotation of the drive nut relative to the housing but prevents a counter-directed rotation. In a similar way, also the ratchet mechanism of the drive nut may comprise e.g. an arc-shaped ratchet member extending in tangential or circumferential direction at the outer circumference of the drive nut.

Also here, the ratchet member may comprise a ratchet tooth to resiliently engage with a correspondingly shaped toothed surface at an inside facing portion of the sidewall of the housing or of a corresponding insert.

For dispensing of a set dose, it is intended that the drive sleeve is axially displaceable relative to the housing for rotatably engaging the drive sleeve and the drive nut. Here, a distal end or a distal face of the drive sleeve is adapted to rotatably engage with an opposite and hence proximal face of the drive nut. Drive nut and drive sleeve therefore comprise mutually corresponding and axially extending positive locking means, such like a mutually corresponding crown wheels in order to transfer angular momentum from the drive sleeve to the drive nut during a dose dispensing procedure.

Typically, the drive sleeve is biased in axial direction relative to the housing by means of one or several spring elements. If the drive sleeve after completion of dose setting procedure is displaced against respective spring forces in distal direction, it may first rotatably engage with the drive nut and it may then consecutively disengaged from the housing. The distally directed displacement of the drive sleeve may therefore disengage the ratchet mechanism by way of which the drive sleeve is rotatably locked to the housing. Once such a release configuration is obtained, the drive sleeve is free to rotate relative to the housing under the effect of the relaxing helical spring.

Since the drive sleeve is operably and rotatably engaged with the drive nut in this release configuration the drive nut rotates accordingly, thereby advancing the piston rod in distal direction. The mutual engagement of the dose limiting member, the drive sleeve and the piston rod remains substantially unaffected by the distally directed displacement of the drive sleeve during mode switching of the drive mechanism.

Since during dose dispensing the drive sleeve rotates in a different and opposite direction compared to a dose setting procedure also the dose limiting member will travel and slide along the piston rod in the opposite, e.g. in distal direction until its distal stop portion engages with the distal stop of the drive sleeve. Since neither the dose limiting member nor the drive sleeve is threadedly engaged with the piston rod, a distally directed relative displacement of the drive sleeve and the dose limiting member relative to the piston rod during a mode switching of the drug delivery device is always possible.

According to another aspect, the invention also relates to a drug delivery device for dispensing of a dose of a medicament. The drug delivery device comprises a drive mechanism as described above and a cartridge at least partially filled with the medicament to be dispensed by the drug delivery. The cartridge is arranged in the housing of the drive mechanism or in a cartridge holder of the drug delivery device which is fixed to the housing either releasably or non-releasably, e.g. in case of a disposable drug delivery device. Consequently, the drug delivery device comprises a cartridge holder to receive and to accommodate a cartridge filled with the medicament.

The cartridge holder may be non-releasably engaged and connected to the proximal housing, e.g. by means of bonding or welding. For reusable drug delivery devices it is of particular benefit when the cartridge holder is detachable from the housing for providing access to the cartridge located therein, in particular for replacing the cartridge. A detachable connection of cartridge holder and housing can be attained by means of mutually corresponding threaded portions of cartridge holder and housing, respectively. Alternatively, it is also conceivable that cartridge holder and proximal housing of the drug delivery device are integrally formed.

Apart from that, the drug delivery device and the drive mechanism may comprise further functional components, such like an actuation member, by way of which a user may operate or manipulate the drug delivery device and its drive mechanism for setting and correcting as well as for dispensing of a correspondingly set dose.

Moreover, the drive mechanism and the drug delivery device may also comprise a dose indicating sleeve, which may rotate together with the drive sleeve and which may provide a visual indication to the user regarding the size of the dose actually set.

In the present context, the distal direction points in the direction of the dispensing and of the device, where, preferably a needle assembly is provided having a double-tipped injection needle that is to be inserted into biological tissue or into the skin of a patient for delivery of the medicament.

The proximal end or proximal direction denotes the end of the device or a component thereof, which is furthest away from the dispensing end. Typically, an actuating member is located at the proximal end of the drug delivery device, which is directly operable by a user to be rotated for setting of a dose and which is operable to be depressed in distal direction for dispensing of a dose.

The drive mechanism particularly serves to displace a piston rod in axial direction for the purpose of dispensing of a dose of a medicament. In addition, the drive mechanism typically comprises components which also form part of and have a function in at least one of the following mechanisms: a dose setting mechanism, a last dose limiting mechanism and a dose indicating mechanism. As will be apparent from the embodiments described herein various components of e.g. the drive mechanism also belong to at least one of the dose setting mechanism, the last dose limiting mechanism and/or to the dose indicating mechanism; and vice versa. Hence, the invention as described herein equally refers to and defines a drive mechanism, a dose setting mechanism, a last dose limiting mechanism and/or a dose indicating mechanism of a drug delivery device.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
Des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, a brief description of the drawings is provided, in which.

DETAILED DESCRIPTION

Figure 2:
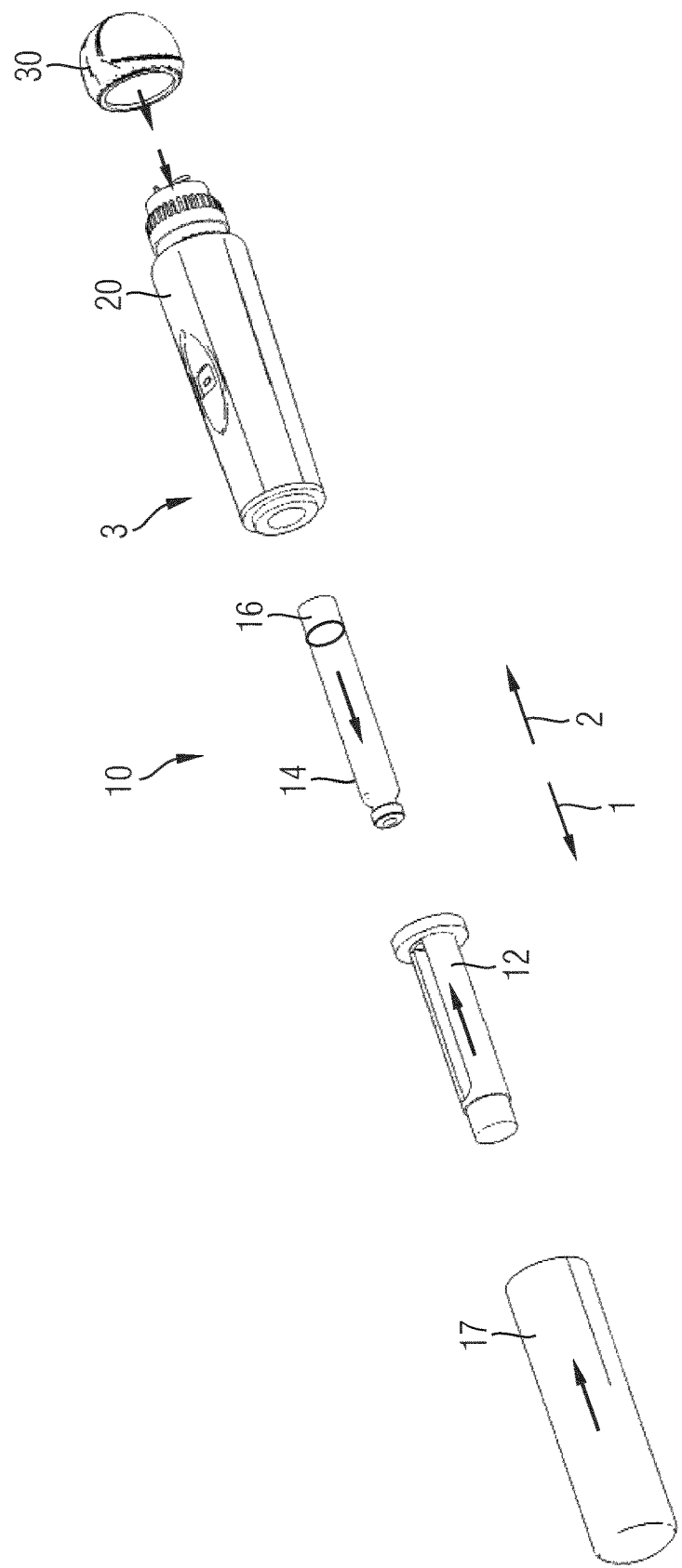
FIG. 2 shows an exploded illustration of the drug delivery device with the drive mechanism assembled in the housing.

In FIG. 2, the drug delivery device 10 is illustrated in an exploded view. The drug delivery device 10 of pen-injector type and comprises a substantially cylindrical and axially elongated shape. Throughout the Figures, the axial distal direction is denoted with reference number 1 and the opposite proximal direction is denoted with reference number 2. The drug delivery device 10 which is also shown in an assembled configuration in FIG. 4 in longitudinal cross section comprises a drive mechanism 3 arranged in a proximal housing 20. In distal direction, the housing 20 is connected with a cartridge holder 12 which is adapted to accommodate and to receive a cartridge 14 containing the medicament to be dispensed by the drug delivery device 10. The cartridge 14 typically comprises a vitreous barrel of cylindrical shape which is sealed in distal direction by a pierceable sealing member, such like a septum.

In proximal direction 2, the cartridge 14 is sealed by a piston 16 slideably arranged in the vitreous barrel of the cartridge 14. Displacement of the piston 16 in distal direction 1 leads to a respective built-up of a fluid pressure inside the cartridge 14. When the distal outlet of a cartridge 14 is connected with e.g. a needle assembly 18, as for instance indicated in FIG. 4, a predefined amount of the liquid medicament contained in the cartridge 14 can be expelled and dispensed via a injection needle of the needle assembly 18, which is not particularly illustrated here.

Figure 4:
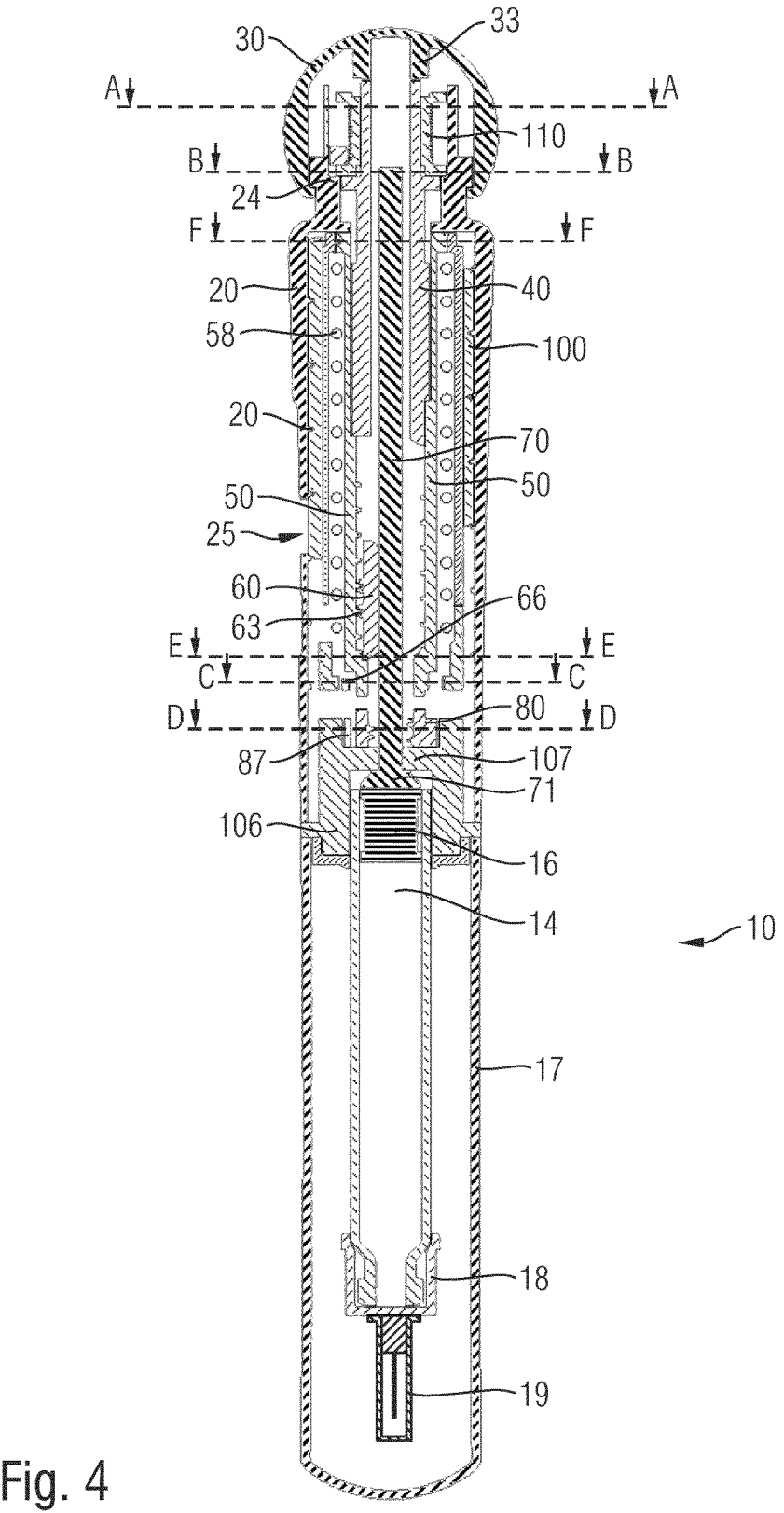
FIG. 4 is illustrative of a longitudinal cross section of the assembled drug delivery device.

In FIG. 4 however, an inner needle cap 19 to protect the double-tipped injection needle is schematically indicated. The needle assembly 18 is typically arranged on a distal end portion of the cartridge holder 14. Typically, a distally located socket of the cartridge holder 12 and the needle assembly 18 comprise mutually corresponding threads to screw the needle assembly 18 onto the cartridge holder 12 in a releasable and removable way.

The cartridge holder 12 is to be protected and covered by a protective cap 17 which is shown in FIGS. 2 and 4. Prior to setting and/or dispensing of a dose, the protective cap 17 as well as the inner needle cap 19 are to be removed. After dispensing or injecting of the medicament into biological tissue, the needle assembly 18 is typically to be discarded and the distal end of the drug delivery is to be covered by the protective cap 17.

The drive mechanism 3 as illustrated in an exploded view in FIG. 3 and as shown in cross section in its fully assembled configuration in FIG. 4 comprises numerous functional components by way of which a dose of variable size can be set and subsequently dispensed.

The dose dispensing procedure comes along with a distally directed advancing displacement of the piston rod 70 relative to the housing 20. The drive mechanism 3 therefore comprises at least a housing 20, a piston rod 70 and a drive sleeve 50 which can be released and operably engaged with the piston rod 70 for selectively setting and dispensing of a dose. Moreover, the drive mechanism 3 comprises a dose limiting member 60 which is engaged with the drive sleeve 50 as well as with the piston rod 70. Mutual engagement of the dose limiting member 60 with both, the drive sleeve 50 and with the piston rod 70 is such, that the dose limiting member is displaced in axial direction, hence in distal and/or proximal direction 1, 2 relative to the drive sleeve 50 when the drive sleeve 50 rotates relative to the piston rod 70 during a dose setting procedure.

Figure 3:
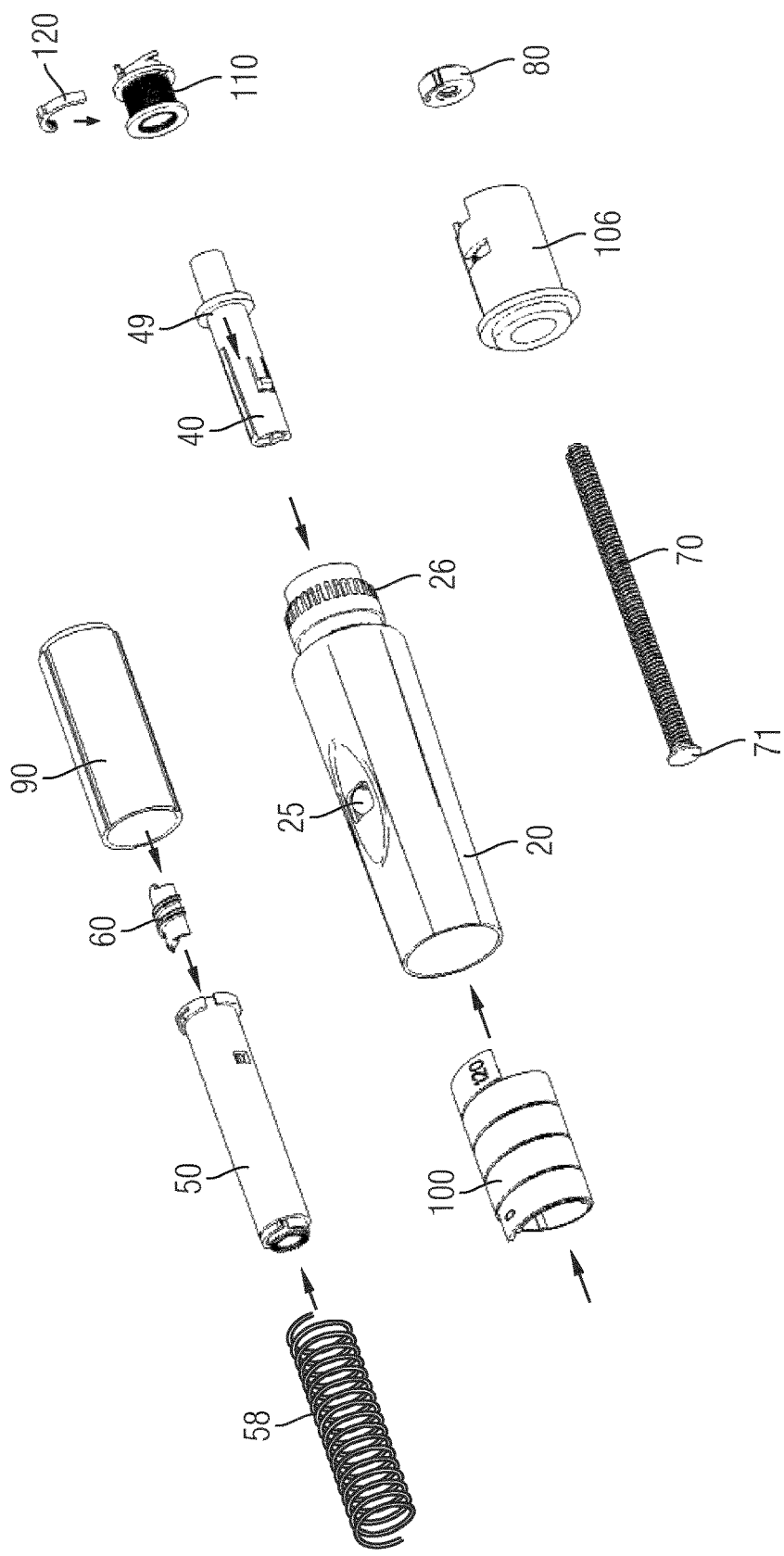
FIG. 3 illustrates various components of the drive mechanism in an exploded view.

Apart from the drive sleeve 50, the dose limiting member 60 and the piston rod 70, the drive mechanism 3 comprises a number of further components as illustrated in FIG. 3. These components together with the actuation member 30 as shown in FIGS. 2 and 4 inter alia serve to visually indicate the size of set dose to a user and further serve to transfer a rotational and/or axial displacement of the user-operated actuation member 30 into respective rotational and/or axial displacement of the drive sleeve 50 for dose setting and/or dose dispensing purpose.

It is to be noted here, the embodiments as illustrated in FIGS. 1 to 20a are only exemplary for one of a plurality of conceivable drive mechanisms that may be equipped with the single dose limiting mechanism as well as the last dose limiting mechanism according to the present invention.

In the following, setting of a dose is described.

Figure 8A:
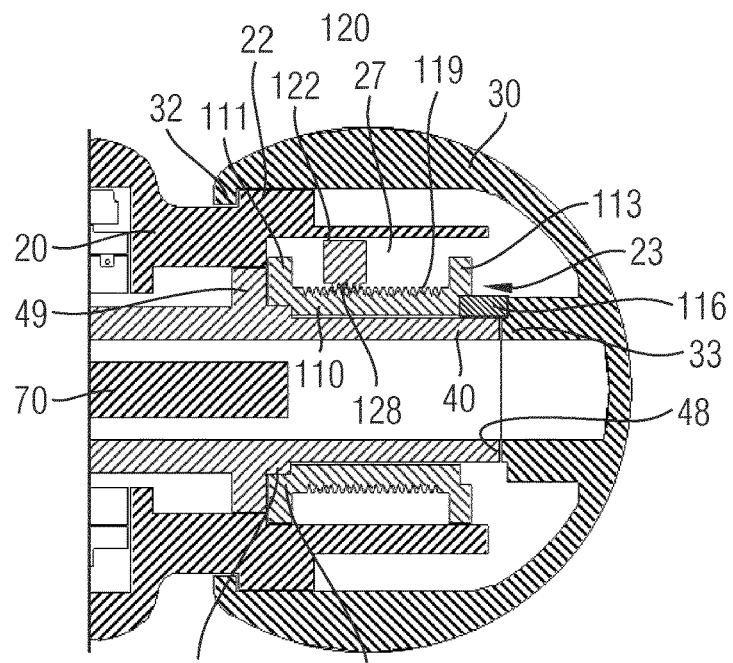
FIG. 8a shows a partial cross section through the proximal end of the drive mechanism during dose setting.
Figure 8B:
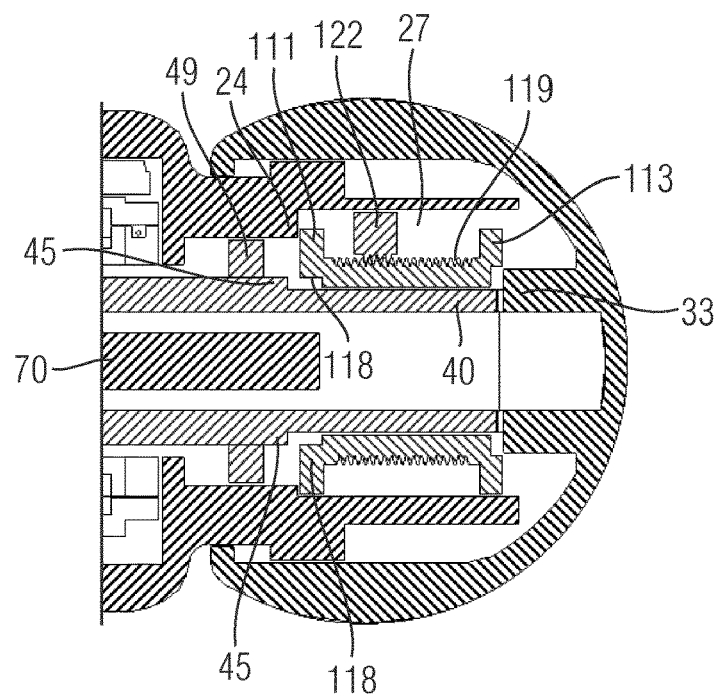
FIG. 8b shows a corresponding cross section during dose dispensing, and FIG. 8c schematically and perspectively illustrates the proximal end of the assembled drive mechanism partially cut, FIG. 9 schematically illustrates the arrangement of the dose limiting member between piston rod and drive sleeve in a perspective and cut view.
Figure 8C:
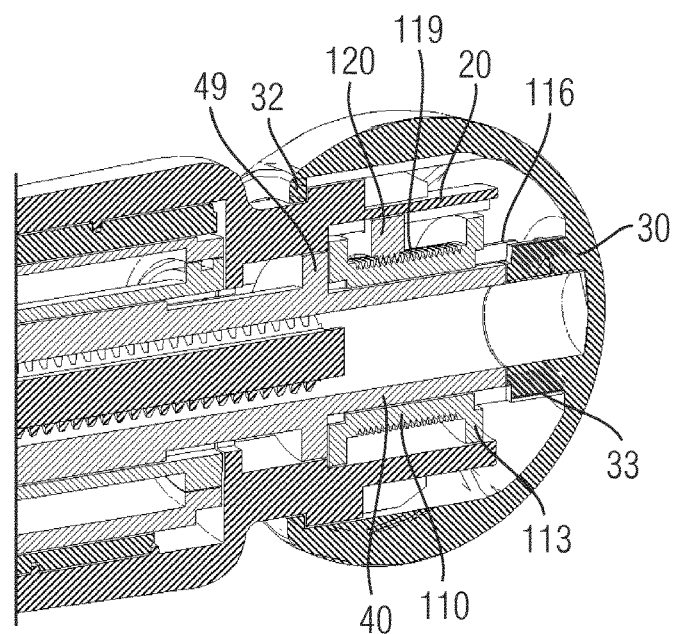
Figure 9:
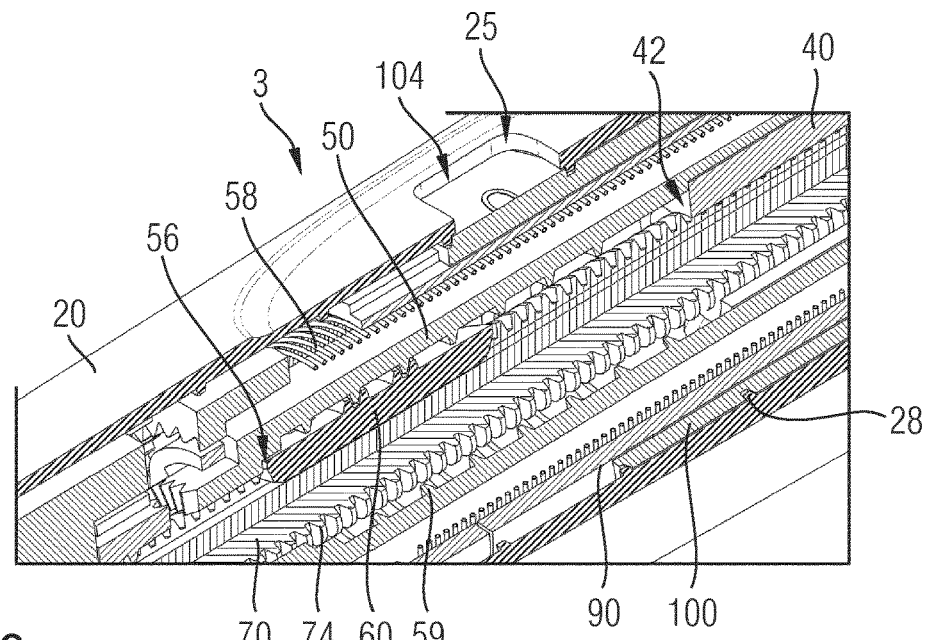
Figure 10A:
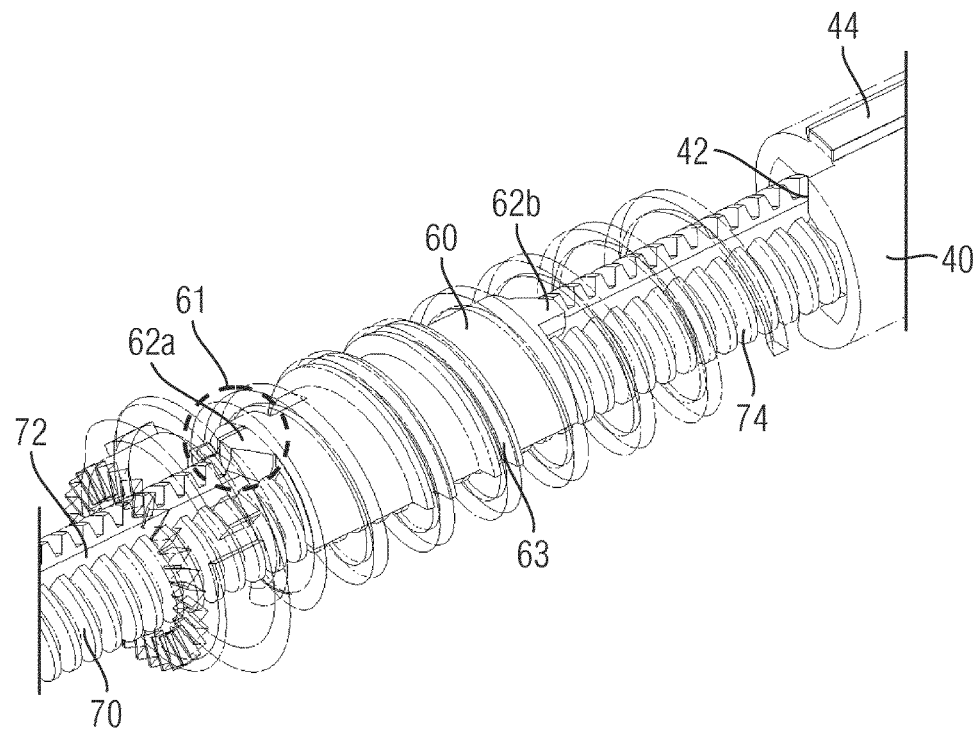
FIG. 10a shows the dose limiting member located on the piston rod in an isolated view.
Figure 10B:
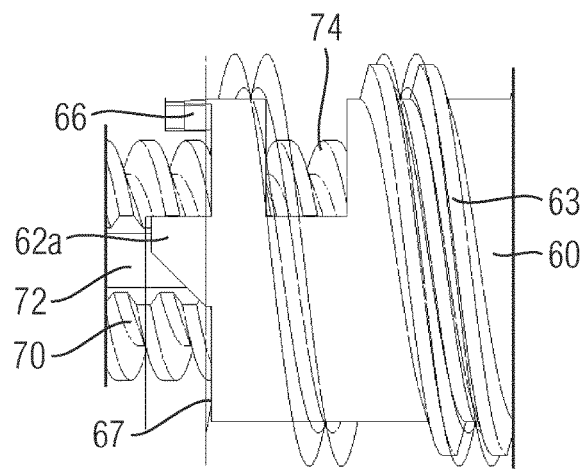
FIG. 10b shows an enlarged view of a distal end of the dose limiting member.

For setting of a dose, the user grips the actuation member 30 located at the proximal end of the housing 20. The actuation member 30 comprises a radially inwardly extending flange portion 32 at its distal end as indicated in FIGS. 8a to 8c, which in a proximally located configuration according to FIG. 8a axially abuts with a radially outwardly extending rim 22 of the housing 20.

The housing 20 further comprises a proximal and tubular shaped receptacle 23 to receive a substantially tubular shaped last dose sleeve 110. The last dose sleeve 110 comprises a radially outwardly extending distal flange 111 extending on a distal end thereof. With this distal flange 111 the last dose sleeve 110 abuts in distal direction with a radially inwardly extending socket 24 of the housing 20. Moreover, by means of the distal flange 111 the last dose sleeve is also radially guided and confined in the proximal receptacle 23 of the housing 20.

Furthermore, by means of its flange portion 32 the actuation member 30 may be snapped on the proximal end of the housing 20 and may therefore positively engage with the housing 20 at least in proximal direction 2. In particular, the actuation member 30 is cup-shaped and surrounds and closes the receptacle 23 of the housing 20 in proximal direction when assembled thereon.

From a proximal portion of the last dose sleeve 110, there extend two helically shaped resilient spring elements 116 integrally formed with the last dose sleeve 110. These spring elements 116 abut with a proximal and inward facing portion of the hollow actuation member 30 and therefore keep the actuation member 30 in its initial, hence proximally located configuration as illustrated for instance in FIG. 8a.

In this initial configuration which coincides with and specifies a dose setting mode of the drive mechanism 3, axially inwardly extending journals 33 of the actuation member 30 extend into two respective diametrically oppositely located recesses 115 of a proximal rim 117 of the last dose sleeve 110. In this way, the last dose sleeve 110 and the actuation member 30 are rotatably coupled in the initial configuration of the actuation member 30 as shown in FIG. 8a as well as in the depressed configuration as shown in FIG. 8b.

In the initial configuration, rotation of the actuation member 30 leads to a corresponding rotation of the last dose sleeve 110. In the dose setting mode, the last dose sleeve 110 is further rotatably engaged and rotatably coupled with a clutch 40 as becomes apparent from a combination of FIGS. 4, 5b and 8a. As in particular illustrated in the cross section B-B in FIG. 5B, the inside facing portion of the distal end of the last dose sleeve 110 comprises a toothed surface 118 that meshes with radially outwardly extending teeth 45 of the clutch 40.

This way, the last dose sleeve 110 and the clutch 40 extending there through and hence providing an axis of rotation for the last dose sleeve 110, are rotatably fixed and are therefore rotatably engaged. Consequently, a rotation of the actuation member 30 leads to an equal rotation of the clutch 40 during a dose setting procedure. The clutch 40 is further connected with the drive sleeve 50. Hence, a distal portion of the clutch 40 is located inside the tubular shaped and hollow drive sleeve 50.

Figure 13:
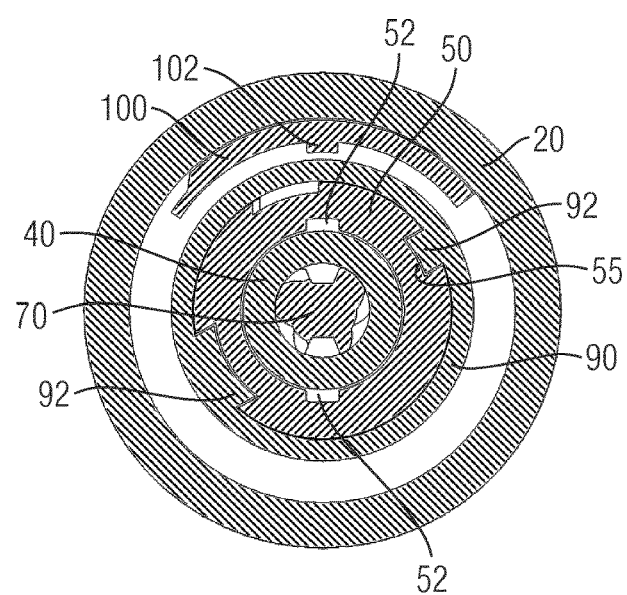
FIG. 13 shows a cross section F-F according to FIG. 4, FIG. 14 perspectively illustrates a dose limiting configuration, wherein the proximal stop portion of the dose limiting member engages with a distal stop of the clutch.
Figure 14:
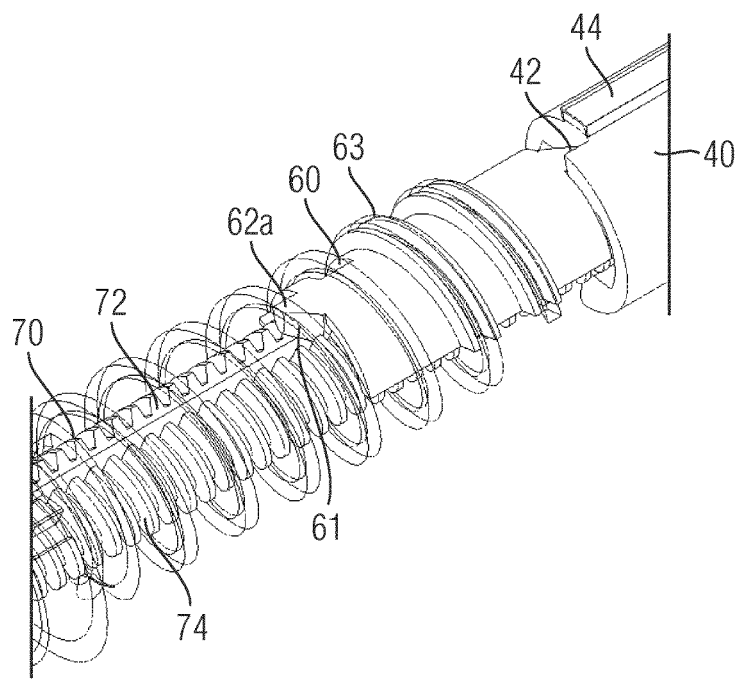
Figure 15:
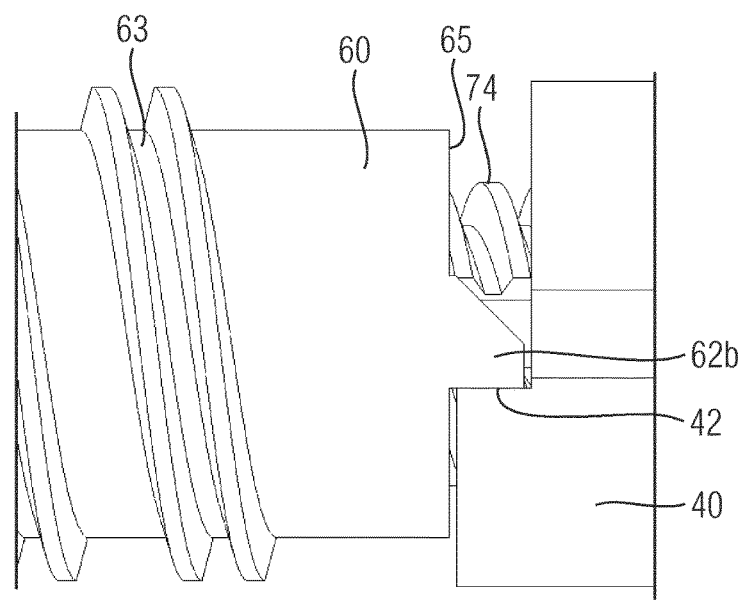
FIG. 15 shows a side view of mutually engaging dose limiting member and clutch according to FIG. 14, FIG. 16a schematically illustrates implementation of a last dose limiting mechanism in an initial configuration

Here, and independent of the mode of operation of the drive mechanism 3, the clutch 40 and the drive sleeve 50 are axially fixed as well as rotatably fixed with respect to each other. Hence, a rotation of the clutch 40 is unalteredly transferred to the drive sleeve 50. Accordingly, also an axial displacement of the clutch 40 is unalteredly transferred to a respective axial displacement of the drive sleeve 50. The drive sleeve as indicated in FIG. 13 comprises two diametrically opposite longitudinal grooves 52 in its inside facing sidewall, as shown in FIG. 13, that are adapted to mate and to receive correspondingly shaped and radially outwardly extending ribs 44 of the clutch 40, as for instance indicated in FIGS. 10a and 14.

Figure 1:
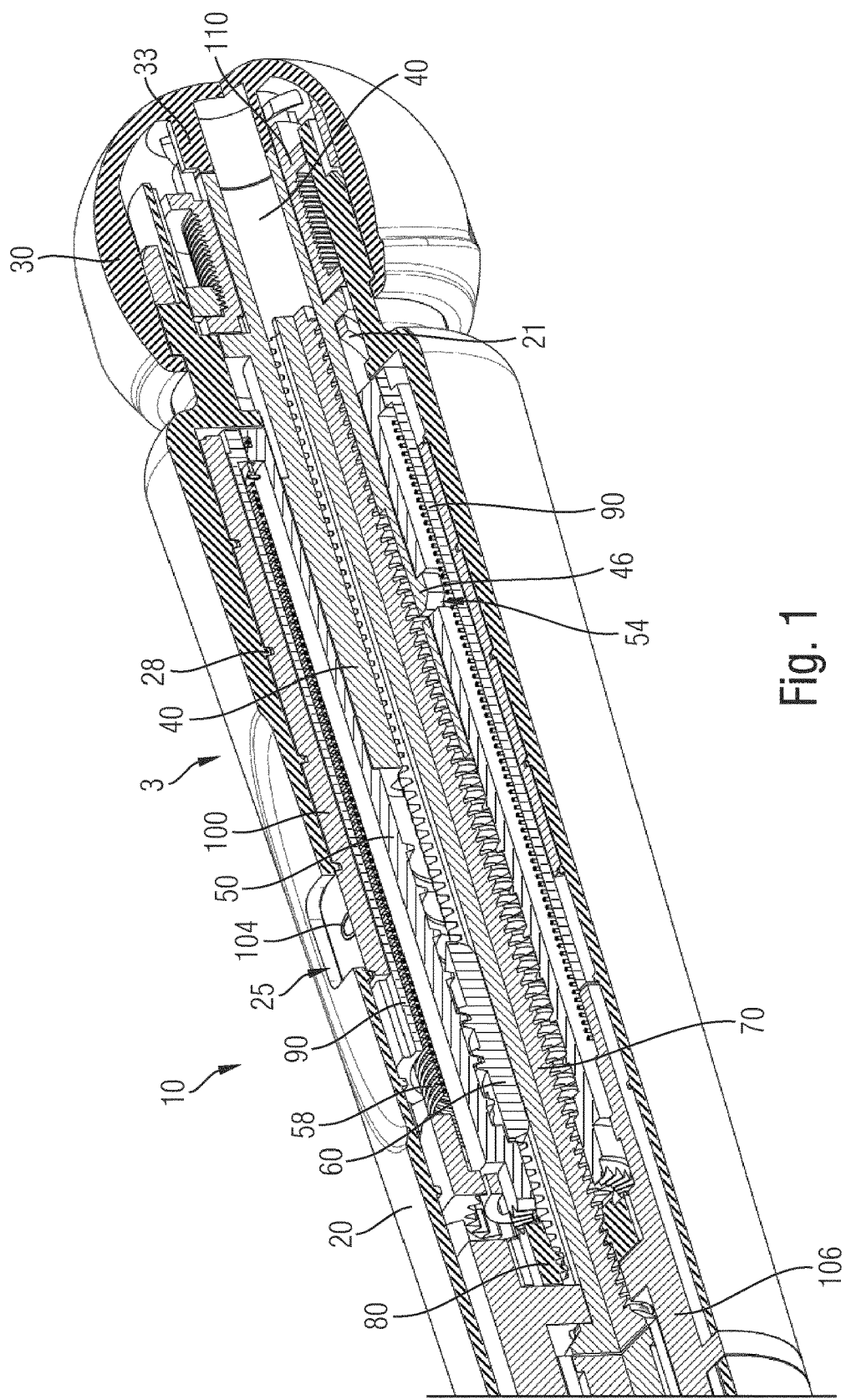
FIG. 1 schematically illustrates the assembled drive mechanism in a partially cut perspective view.

Moreover, the clutch 40 comprises at least one, preferably at least two oppositely located radially outwardly extending and resiliently deformable snap portions 46 adapted to engage with a correspondingly shaped recess 54 of the drive sleeve 50 as schematically illustrated in FIG. 1. By means of the mutually corresponding ribs 44 and grooves 52 as well as due to the snap portions 46 engaged with the recess 54, a rotational and longitudinal engagement of clutch 40 and drive sleeve 50 can be attained.

The drive sleeve 50 can be rotated inside and relative to the housing 20 in a dose incrementing direction against the action of a helical spring 58. One end, e.g. the proximal end of the helical spring 58 is attached and coupled to the proximal end of the drive sleeve 50 while an opposite, e.g. distal end of the helical spring 58 is fastened to the housing 20. A dose incrementing rotation of the actuation member 30 therefore leads to a corresponding rotation of the drive sleeve 50 against the restoring force of the helical spring 58 almost completely surrounding the drive sleeve 50.

The drive sleeve 50 further comprises an arc-shaped ratchet member 51 near a distal end thereof. The ratchet member 51 is resiliently deformable in radial direction and comprises a radially outwardly extending tooth or nose 53 mating with a correspondingly shaped toothed profile 108 of an insert 106 located inside and fix to the housing 20.

In this context it is to be noted, that the insert 106 could also be integrally formed with the housing 20. It is predominately due to the assembly and manufacturing process that the insert 106 is provided as a separate part to be assembled in the housing 20.

Figure 6A:
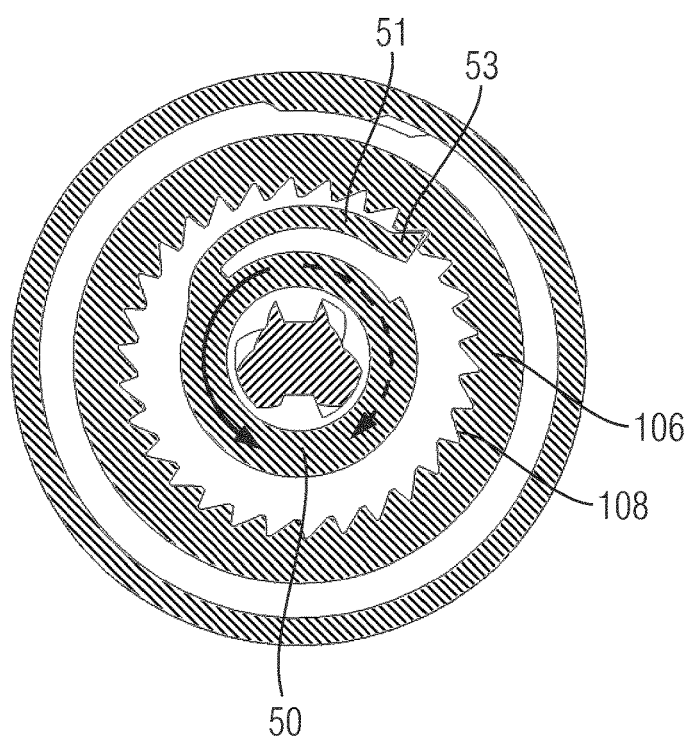
FIG. 6a shows a cross section through C-C according to FIG. 4.
Figure 6B:
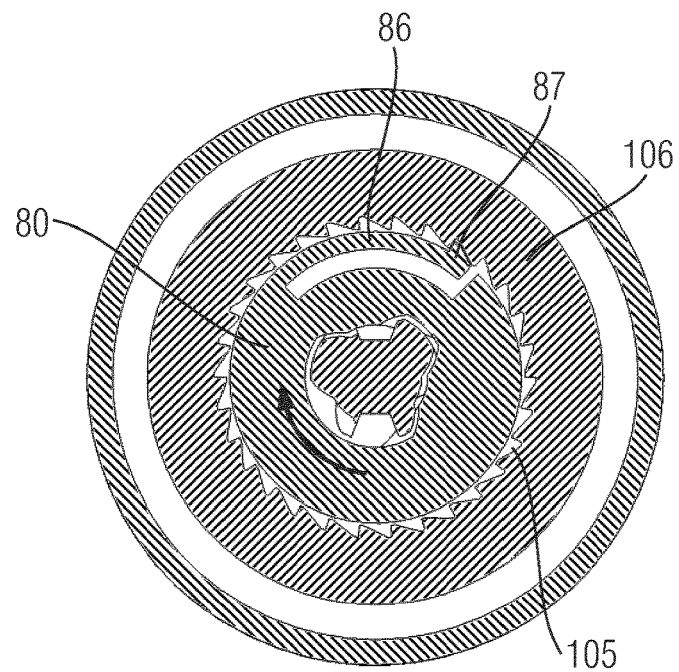
FIG. 6b shows a cross section D-D according to FIG. 4, FIG. 7a schematically shows the position of the drive sleeve relative to the drive nut during a dose setting procedure.

As indicated in the cross section C-C according to FIG. 6a, the tooth 53 provided at a free end of the resiliently deformable ratchet member 51 meshes with the toothed surface 108 of the insert 106 when rotating counter clockwise, hence during a dose incrementing rotation of the drive sleeve 50. Here, passing of the tooth 53 along the toothed surface 108 generates an audible feedback to the user, indicating, that the dose is stepwise incremented.

The geometry of the toothed surface 108 and the tooth 53 is designed such, that the spring force arising from the helical spring 58 and acting in opposite, hence clockwise direction on the drive sleeve 50 is not large enough to rotate the drive sleeve 50 in the opposite, hence clockwise sense. This way, mechanical energy can be stored by the helical spring 58 which is to be released only on demand during a subsequent dose dispensing procedure.

Even though not particularly illustrated here, the toothed surface 108 and the ratchet member 51 engage in such a way, that a dose decrementing rotation of the drive sleeve 50 is indeed possible, e.g., when a user exerts a respective counter-directed angular momentum to the actuation member 30, which exceeds the resilient resistance provided by the mutually engaged ratchet member 51 and the toothed surface 108.

A dose incrementing action governed by a rotation of the actuation member 30 and a corresponding rotation of the drive sleeve 50 also leads to a corresponding rotation of a dose indicating sleeve 100. The dose indicating sleeve 100 is threadedly engaged with the housing 20 and comprises numerous dose indicating numbers 104 at its outer circumference, as for instance indicated in FIG. 3. The numbers are arranged in a helical way on the outer circumference of the dose indicating sleeve 100. Moreover, the dose indicating sleeve 100 is threadedly engaged with the inside facing sidewall portion of the housing 20 as becomes apparent from the inner thread 28 of the housing 20 as for instance indicated in FIG. 1.

A rotation of the drive sleeve 50 unalteredly transfers to a respective rotation of the dose indicating sleeve 100 via the engagement of an intermediate sleeve 90. The intermediate sleeve 90 is sandwiched in radial direction between the drive sleeve 50 and the dose indicating sleeve 100. Hence, the intermediate sleeve 90 surrounds the drive sleeve 50 and is further rotatably coupled with the drive sleeve 50 at a proximal end portion as indicated in FIG. 13. As illustrated there, the drive sleeve 50 is splined to the intermediate sleeve 90. The drive sleeve 50 comprises two oppositely disposed radially inwardly extending recesses 55 to receive correspondingly shaped radially inwardly extending protrusions 92 of the intermediate sleeve 90.

Figure 12:
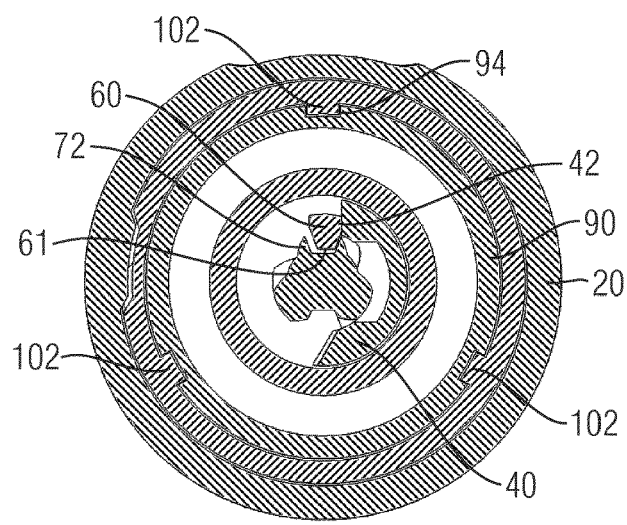

As indicated further in the cross section according to FIG. 12 the intermediate sleeve 90 is also splined with its outer circumference to the dose indicating sleeve 100. Hence, the intermediate sleeve 90 comprises three circumferentially distributed and radially inwardly extending recesses 94 as its outer circumference to receive correspondingly shaped and radially inwardly extending protrusions 102 of the dose indicating sleeve 100. The dose indicating sleeve 100 is threadedly engaged with the housing 20 and is therefore axially engaged with respect to the housing. However, the splined engagement of the intermediate sleeve 90 with the dose indicating sleeve 100 allows for an at least limited sliding axial displacement between the dose indicating sleeve 100 and the intermediate sleeve 90, in particular during a mode switching of the drive mechanism 3.

Since the intermediate sleeve 90 may be axially displaceable relative to the dose indicating sleeve 100 intermediate sleeve 90 and drive sleeve 50 could also be integrally formed, thereby reducing the number of parts and components the drive mechanism is made of.

When during a dose setting procedure the actuation member 30 is rotated relative to the housing the drive sleeve 50 is rotated in the same way and due to the two-fold splined engagement of drive sleeve 50, intermediate sleeve 90 and dose indicating sleeve 100 also the dose indicating sleeve 100 will always instantly show a corresponding dose size indicating number 104, e.g. representing an amount of international units (I.U.) in a dose displaying window 25 of the housing 20. As indicated for instance in FIG. 9, the dose indicating window 25 may comprise a recess or a through opening in the sidewall of the housing 20.

Decrementing of the dose, hence dialing the actuation member 30 in an opposite sense of rotation, leads to a respective counter-rotation of the drive sleeve 50. Consequently, also the intermediate sleeve 90 and the dose indicating sleeve 100 rotate in the opposite sense and a correspondingly decreasing dose indicating number will show up in the window 25.

In an alternative embodiment, the inner thread 28 of the housing 20 may only be provided at a portion of the inside facing sidewall of the housing 20 which is located proximal from the dose indicating window 25. Said housing portion proximally offset from the dose indicating window 25 may either comprise a positive or negative threaded portion. Hence, it may either comprise a helically extending groove or a radially inwardly extending helically extending protrusion. As a consequence, the dose indicating sleeve only has to provide a correspondingly shaped threaded portion at its proximal end. In this way, a distal portion of the dose indicating sleeve may be free of threads, grooves or protrusions.

In the following dispensing of a dose is described.

Once a dose has been correctly set, the drive mechanism 3 may be switched into a dispensing mode by depressing the actuation member 30 in distal direction 1 as for instance indicated in FIG. 8b. Hence, the actuation member 30 fulfils a double or even a triple function. First of all, the actuation member 30 serves to transfer an angular momentum to the last dose sleeve 110 and/or to further functional components of the drive mechanism 3 operably engaged therewith. Second, the actuation member 30 controls and triggers a dose dispensing procedure. Third, the actuation member 30 actually seals and closes a proximal end of the housing 20 of the drive mechanism 3 and/or of the drug delivery device 10.

Moreover, the present arrangement of the actuation member 30 also allows for a priming of the drive mechanism 3 during manufacturing of the drug delivery device 10, when a cartridge 14 is to be readily arranged therein. In the process of assembly of the device 10, the piston rod 70 can be advanced in distal direction 1 to directly abut with the piston 16 of the cartridge 14. Here, a proximal end of the piston rod 70 is accessible, e.g. by means of a separate push rod, which is actually not illustrated here. It is then after bringing the piston rod 70 in operative engagement with the piston 16 of the cartridge 14 that the actuation member 30 is finally assembled to the housing 20 thereby closing the proximal receptacle 23 thereof.

By displacing the actuation member 30 in distal direction 1, the resilient spring elements 116 of the last dose sleeve 110 will be compressed. At the same time, the axially inwardly protruding journals 33 of the actuation member 30 will further extend through the longitudinal recesses 115 of the last dose sleeve 110 and will push a proximal rim 48 of the clutch 40 in distal direction 1 as becomes apparent from a comparison of FIGS. 8a and 8b.

Figure 5A:
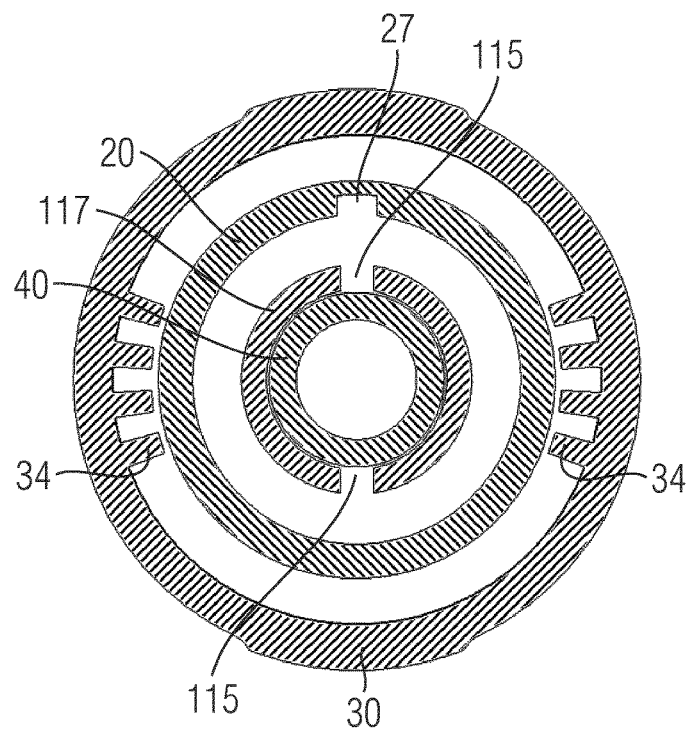
FIG. 5a shows a cross section along A-A of FIG. 4.
Figure 5B:
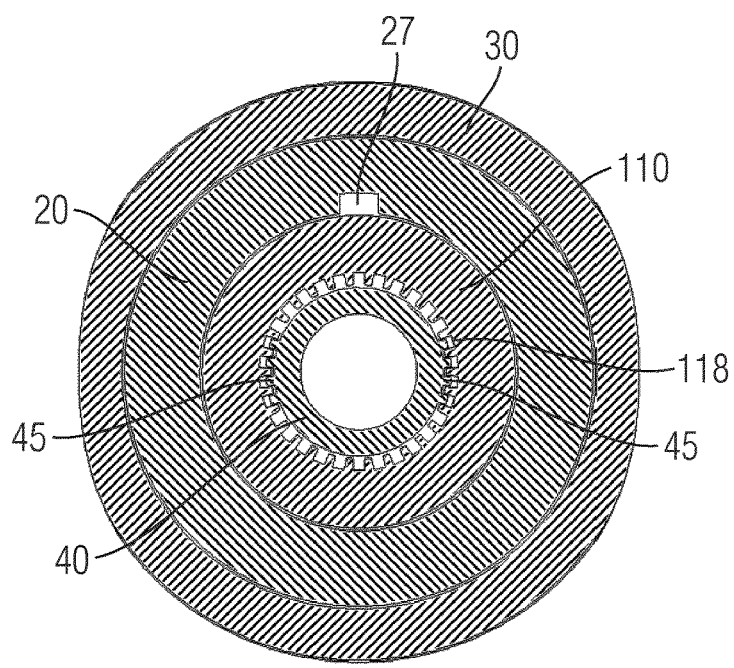
FIG. 5b shows a cross section along B-B according to FIG. 4.

Due to this distally directed displacement of the clutch 40, radially outwardly extending teeth 45 of the clutch 40, as shown in FIG. 5b, do no longer engage with the inner toothed surface 118 of the last dose sleeve 110. As a consequence, the clutch 40 is rotatably disengaged from the last dose sleeve 110 and is free to rotate.

At the same time radially inwardly extending teeth 34 provided at the inside facing sidewall portion of the actuation member 30 engage with a toothed ring 26 provided on the outer circumference of the proximal portion of the housing 20. Since the teeth 34 get in engagement with the toothed ring 26 by the axial and distally directed displacement of the actuation member 30 relative to housing 20, the actuation member 30 is rotatably locked to the housing 20 during a dose dispensing action. Consequently, the last dose sleeve 110, which is still rotatably engaged with the actuation member 30, cannot rotate during the dose dispensing procedure.

Since the clutch 40 is not only rotatably but also axially coupled and connected with the drive sleeve 50, the distally directed displacement of the clutch 40 is substantially unalteredly transferred to a respective distally directed displacement of the drive sleeve 50.

As further indicated in FIG. 1, the clutch 40 is biased in proximal direction 2 by means of at least one spring element 21, which is preferably integrally formed with the housing 20. The spring element 21 can be resiliently deformed and biased in axial, hence distal direction 1 by the radially extending flange 49 of the clutch 40. Since the clutch 40 is only to be displaced in distal direction 1 against the action of the spring element 21, the coupling of the drive sleeve 50 with a drive nut 80 is only active as long as a respective distally directed force is applied to the actuation member 30, e.g. during a dose dispensing procedure.

Figure 7A:
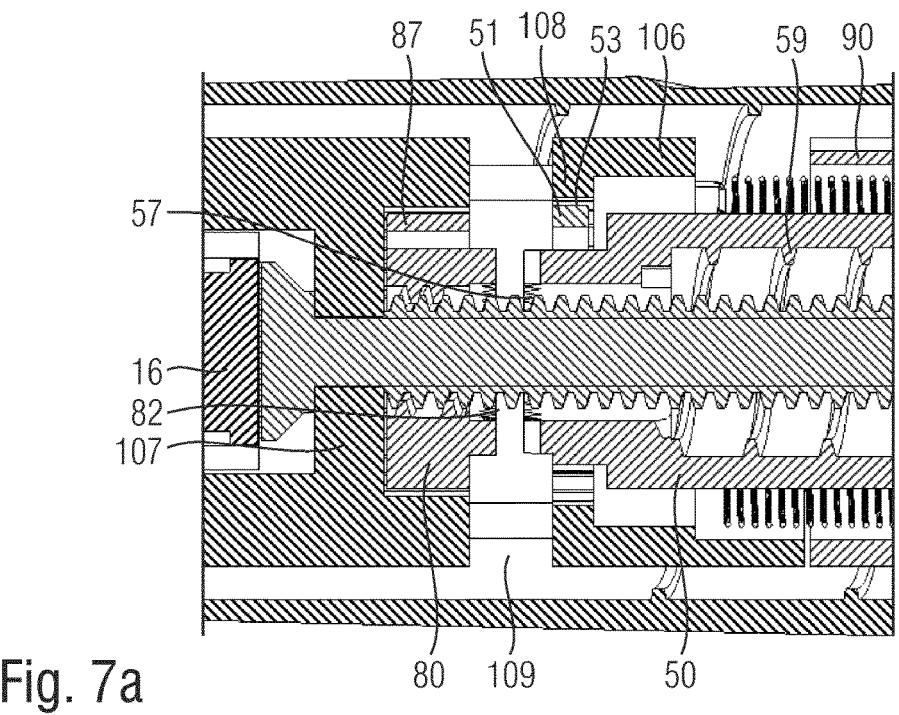
FIG. 7b shows an operable engagement of drive sleeve and drive nut during a dose dispensing procedure.
Figure 7B:
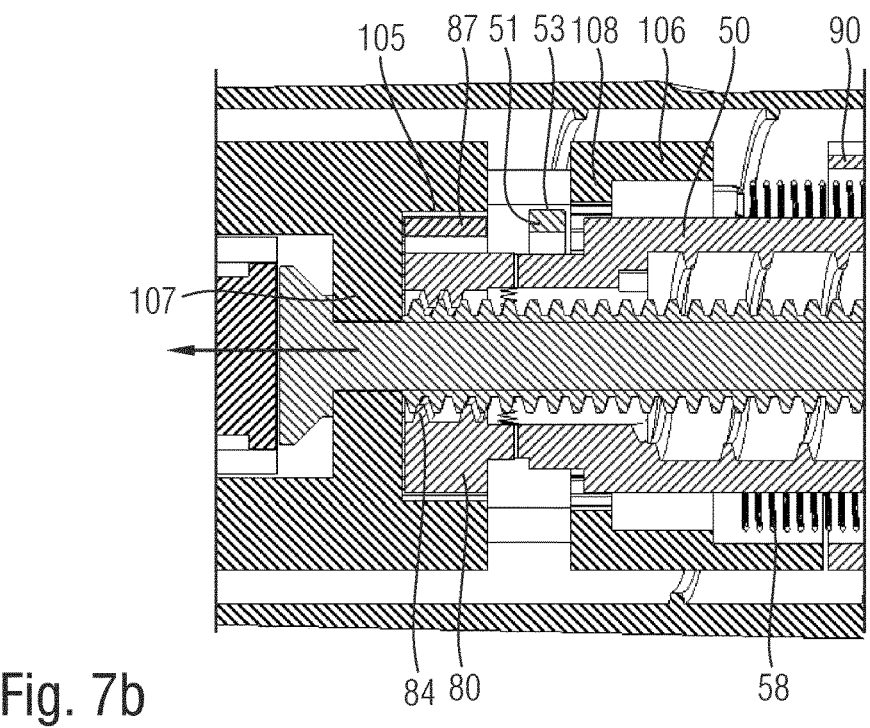

The distally directed displacement of the drive sleeve 50 is limited by the drive nut 80 as illustrated in cross section in FIGS. 7a and 7b. When in mutual axial abutment as indicated in FIG. 7b, the drive sleeve 50 and the drive nut 80 are rotatably engaged while the drive sleeve 50 and its ratchet member 51 is disengaged from the tooted surface 108 of the insert 106. Mutual rotatable engagement of drive sleeve 50 and drive nut 80 is achieved by mutually corresponding teeth or comparative interlocking members provided on a distal face 57 of the drive sleeve 50 and on a proximal end face 82 of the drive nut 80, respectively. The proximal face 82 of the drive nut 80 may comprise a crown wheel operable to engage with a correspondingly shaped crown wheel provided on the distal face 57 of the drive sleeve 50.

Preferably, the axial extension of mutually corresponding crown wheels or spur gears located on the proximal face 82 and on the distal face 57 is such, that a rotational engagement of drive sleeve 50 and drive nut 80 is achieved before the ratchet member 51 of the drive sleeve 50 is released from the toothed surface 108 of the insert 106 during a distally directed displacement of the drive sleeve 50. In this way, a substantially slipless coupling of drive sleeve 50 and drive nut 80 can be achieved.

An early or premature release of the actuation member 30 prior to a termination of the dose dispensing procedure will lead to an immediate proximally directed displacement of the clutch 40 relative to the housing 20 under the effect of the biased spring element 21. Consequently, the ratchet member 51 of the drive sleeve 50 will reengage with the toothed surface 108 of the insert 106 for keeping the energy stored in the biased helical spring 58.

The drive nut 80 is preferably axially fixed in the insert 106. As indicated in FIGS. 7a and 7b, the insert 106 may comprise a circumferential or punctual recess 109 to receive an axially acting fastening member for the drive nut 80.

The insert 106 further comprises two diametrically oppositely arranged and radially inwardly extending protrusions 107 that engage with correspondingly shaped grooves 72 of the piston rod 70. The piston rod 70 extends through the insert 106 in axial direction and comprises a pressure foot 71 at its distal end to directly engage with the piston 16 of the cartridge 14. The radially inwardly extending protrusions 107 of the insert 106 may further be part of a web or flange portion featuring a through opening, through which the piston rod 70 extends axially. The pressure foot 71 may be rotatable with respect to the piston rod 70. But when the piston rod 70 is non-rotatably engaged with the housing 20, the rotatably supported pressure foot 71 is not required in general.

The piston rod 70 comprises an outer thread 74 which is only threadedly engaged with an inner thread 84 of the drive nut 80.

When rotatably coupled, the drive sleeve 50 under the action of the biased helical spring 58 transfers an angular momentum to the drive nut 80, which in turn rotates around the axially fixed piston rod 70. The rotation of the drive nut 80 then serves to advance the piston rod 70 in distal direction 1 for expelling of a dose of the medicament.

Moreover, in the distal stop position as illustrated in FIG. 7b, the ratchet member 51 of the drive sleeve 50 may audibly engage with another toothed inner surface of the insert 106 or housing 20, respectively which is located distally offset from the toothed surface 108. In this way a dose decrementing rotation of the drive sleeve 50 during dose dispensing may generate an audible feedback for the user that a dose dispensing procedure is actually in progress.

The drive nut 80 also comprises a ratchet member 86 having a circumferentially extending arm resiliently deformable in radial direction. At the free end of the ratchet member 86 a radially outwardly extending tooth 87 is located which is adapted to mesh with a correspondingly shaped toothed surface 105 provided at the inside facing wall of the insert 106. As indicated in cross section in FIG. 6b the ratchet member 86 and the toothed surface 105 are configured such, that only a clockwise, hence a dose dispensing rotation of the drive nut 80 is allowed while a counter-directed rotation of the drive nut 80 is effectively inhibited. This way, the piston rod 70 is only displaceable in distal direction 1 but not in proximal direction with respect to the housing. The ratchet member 86 of the drive nut 80 and the toothed surface 105 of the insert 106 provide an effective anti-backup feature.

Moreover, when rotating in a dose decrementing direction during a dose dispensing procedure, the ratchet member 86, and in particular its radially outwardly extending free end consecutively meshes with the geared or toothed profile of the insert 106 or with a correspondingly shaped inner surface portion of the housing 20. The mutual engagement of the ratchet member 86 sliding along the toothed surface 105 also generates an audible click sound inherently indicating to the user, that the dispensing procedure is actually in progress.

For limiting a dose setting as well as a dose dispensing procedure the drive mechanism 3 further comprises a dose limiting member 60 slideably arranged on the piston rod 70 in axial direction and threadedly engaged with the drive sleeve 50. The dose limiting member 60 comprises the shape of a half-shell and therefore only partially surrounds the piston rod 70 in circumferential or tangential direction. The dose limiting member 60 comprises a radially inwardly extending gliding portion 61 by way of which the dose limiting member 60 may slide or glide along the groove 72 of the piston rod 70. Due to the this mutual engagement of the gliding portion 61 and the groove 72 of the piston rod 70, the dose limiting member 60 is rotatably fixed to the piston rod 70. In other words the dose limiting member 60 is splined to the piston rod 70 or is keyed engaged with the piston rod 70.

The dose limiting member 60 further comprises an external thread 63 at its outer circumference to engage with a correspondingly shaped internal thread 59 of the drive sleeve 50. In this way, the dose limiting member 60 is displaced axially with respect to the piston rod 70 as well as with respect to the drive sleeve 50 when the drive sleeve 50 rotates relative to the piston rod 70, in particular during a dose setting procedure.

During such a dose dispensing procedure, the drive sleeve 50 rotates in an opposite direction and hence the dose limiting member 70 experiences an oppositely directed axial displacement relative to the piston rod 70 and relative to the drive sleeve 50.

Typically, during a dose setting procedure, the dose limiting member is displaced in proximal direction 2 towards the clutch 40. During a dose dispensing procedure, the dose limiting member 60 is displaced in the opposite direction, hence in distal direction 1 towards the drive nut 80.

At its proximal end the dose limiting member 60 comprises a proximal stop portion 62b extending from a proximal end face 65 of the dose limiting member 60 in axial, hence proximal direction 2.

The proximal stop portion 62b is adapted to abut with a correspondingly shaped and correspondingly oriented radially extending stop 42 provided at a distal end of the clutch 40. Such an abutment configuration is for instance shown in FIGS. 14 and 15. By means of the mutual abutment of the proximal stop portion 62 of the dose limiting member 60 with the stop 42 located at the distal end of the clutch 40, a further rotation of the drive sleeve 50 as well as of the clutch 40 relative to the piston rod 70 can be effectively inhibited.

Since the proximal stop portion 62b of the dose limiting member 60 abuts in radial and circumferential direction with the clutch 40, any further rotation of the clutch 40 and hence any further rotation of the drive sleeve 50 rotatably coupled therewith is effectively blocked. Moreover, the clutch 40 also provides a proximal stop for the dose limiting member 60. Due to the threaded engagement of the dose limiting member 60 and the drive sleeve 50, also here, a further rotation of the drive sleeve 50 exceeding a predefined maximum single dose configuration can be prevented.

In this way, the dose limiting member 60 serves to provide a single dose limiting mechanism which is operable to effectively inhibit setting of a dose exceeding a predefined maximum single dose, e.g. 120 I.U. of insulin.

Figure 11:
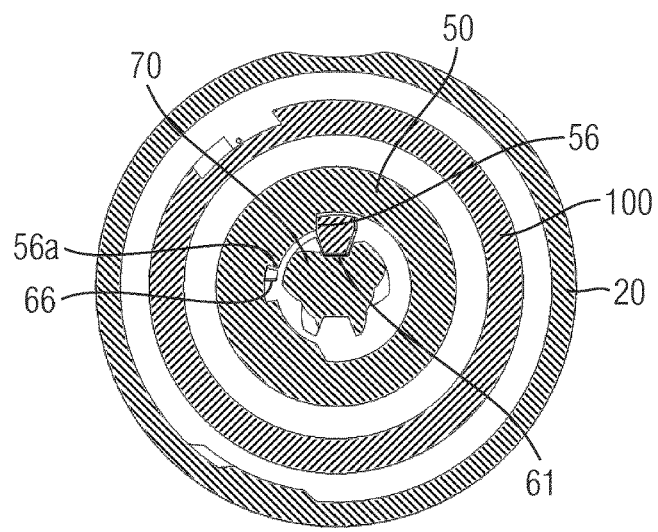
FIG. 11 is a cross section along E-E according to FIG. 4, FIG. 12 schematically illustrates a cross section through the drive mechanism when the dose limiting member engages and radially abuts with the clutch.

The dose limiting member 60 also comprises a distal stop portion 62a extending accordingly in distal direction 1 from a distal end face 67 of the dose limiting member 60. Here, the distal stop portion 62a may accordingly engage with a radially inwardly and axially extending stop 56 of the drive sleeve 50. The corresponding distal stop 56 of the drive sleeve is apparent from FIGS. 19a and 20a. Additionally, the radially inwardly and axially extending stop 56 of the drive sleeve 50 is shown in FIG. 11 in an abutment configuration with the dose limiting member 60.

The position and orientation of the distal stop portion 62a and the stop 56 is selected such, that a mutual abutment of distal stop portion 62a and stop 56 is correlated with a zero dose configuration at the end of a dose dispensing procedure, i.e. when the dose indicating sleeve 100 has returned into its initial position.

Since the rotation of the drive sleeve 50 can be blocked and interrupted by the dose limiting member 60 in both directions, i.e. in a dose setting mode as well as in a dose dispensing mode, further stop features to inhibit a dose incrementing or dose decrementing rotation of the drive sleeve 50 are generally not required. As a consequence, even the dose indicating sleeve 100 and its arrangement in the housing 20 can be provided without any further rotation limiting means.

As shown in FIGS. 10b and 19 to 20a, the distal stop portion 62a of the dose limiting member 60 is further equipped with a clicking member 64 which is adapted to generate an audible sound before or when the distal stop portion 62a engages with the stop 56 of the drive sleeve 50. The clicking member 64 comprises a resilient arm 68 extending in circumferential direction from the distal stop portion 62a. At its free end the arm 68 comprises a latch portion 66 featuring a tooth-like shape with a slanted or tilted leading surface. During a dose dispensing procedure and well before reaching the distal stop configuration, the latch portion 66 engages with the stop 56 and becomes subject to a axially, hence proximally directed evasive movement due to the resilient deformability of the arm 68.

Figure 20:
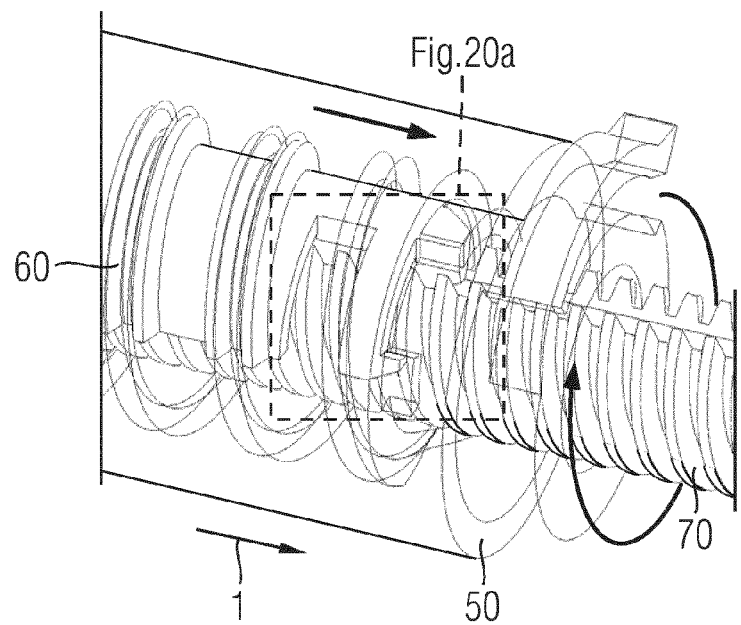
FIG. 20a shows an enlarged framed section of FIG. 20.
Figure 20A:
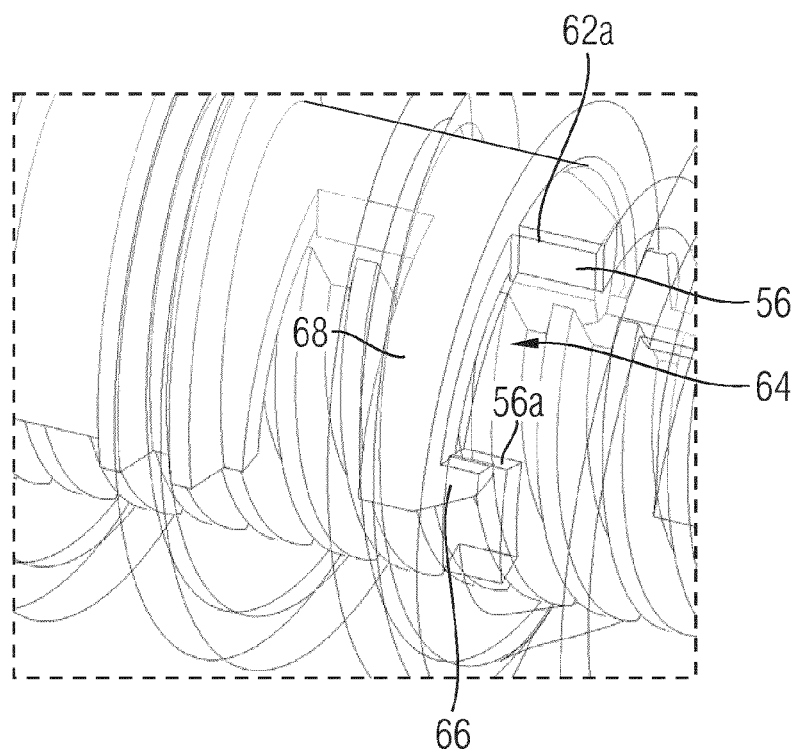

In the final stop configuration as indicated in FIGS. 20 and 20a, the latch portion 66 may relax and may snap into a recess 56a provided at the inside wall of the drive sleeve 50, thereby generating an audible click sound. The returning of the latch portion 66 and the resilient arm 68 into its initial unbiased configuration may occur before the distal stop portion 62a engages with the stop 56 or it may coincide with the stop configuration, thereby audibly indicating to a user, that the dose dispensing procedure is close to end or has just terminated. Said audible feedback is not only obtained at the end of a dose dispensing procedure but also when a zero dose size, e.g. 0 I.U., is set by means of a dose correction procedure.

Figure 19:
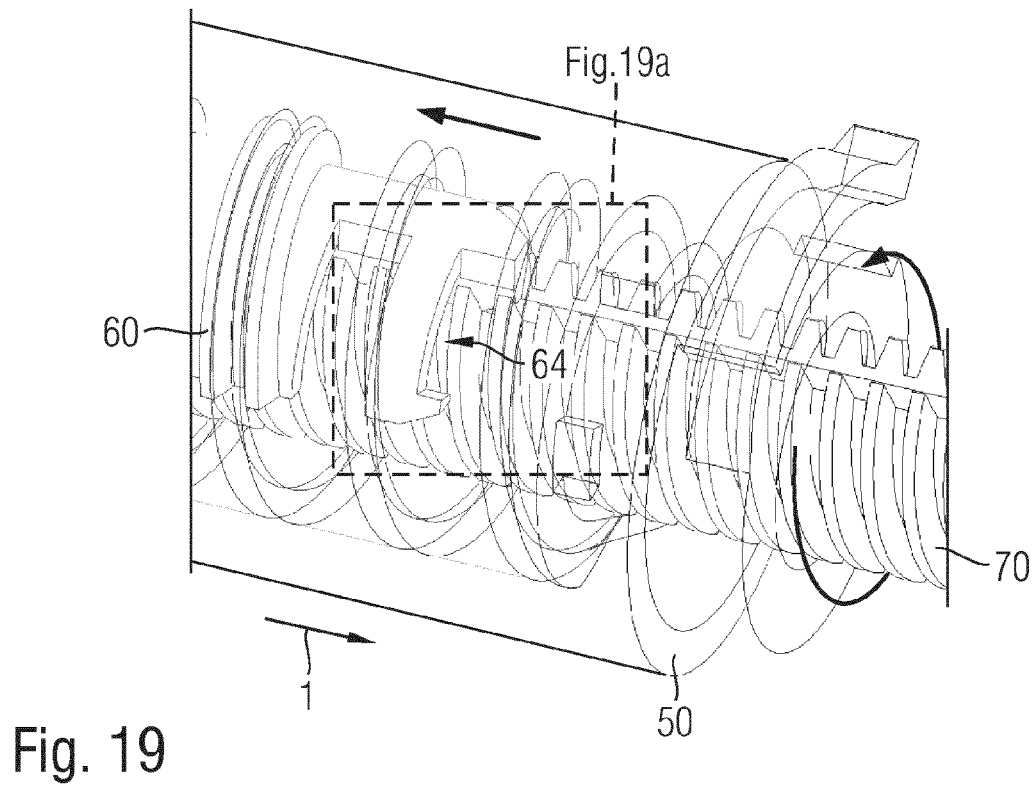
Figure 19A:
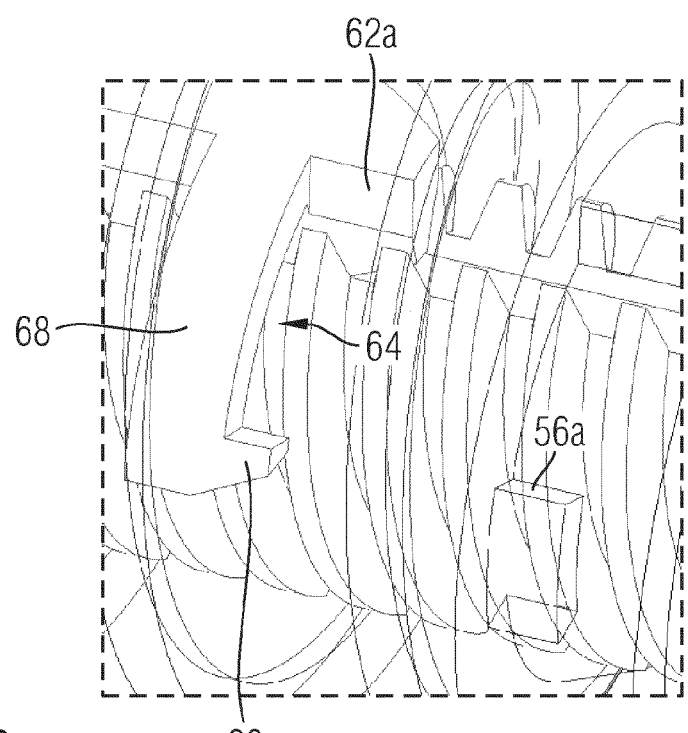

In FIGS. 19 and 19a, the stop 56 and the circumferentially offset recess 56a are illustrated after the dose limiting member 60 has been displaced in proximal direction 2. It is apparent from FIGS. 19a and 20a as well as from FIG. 10b, that the distal stop portion 62a axially protrudes from the axial end of the latch portion 66. Since the axial height of the latch portion 66 is slightly smaller than that of the trailing distal stop portion 62a, the latch portion 66 and the clicking member 64 does not substantially affect the operability of the drive mechanism. The cross section E-E according to FIG. 11 further illustrates the coincidence of the latch portion 66 engaging with the recess 56a and the distal stop portion 62a engaging with the stop 56 of the drive sleeve 50.

Figure 16A:
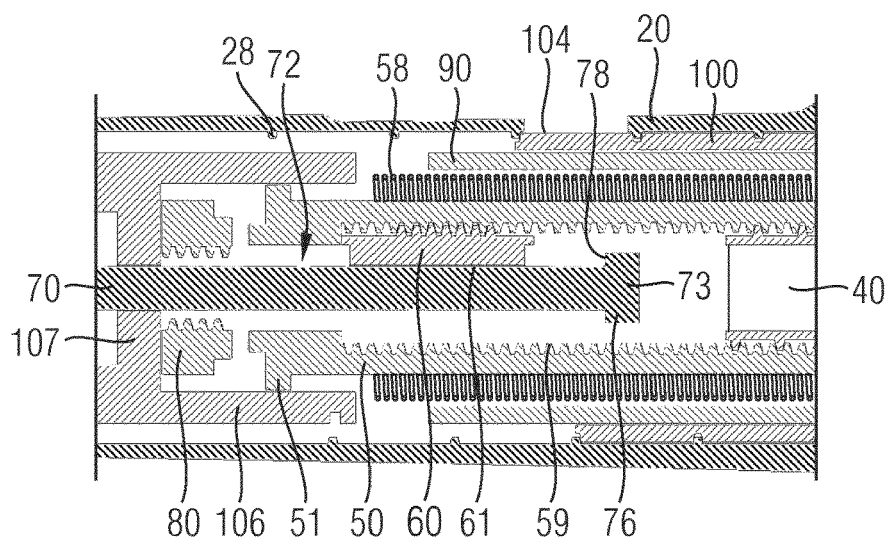
FIG. 16b shows the last dose limiting mechanism in a last dose limiting configuration, FIG. 17a perspectively shows a last dose sleeve in an isolated perspective illustration.

The dose limiting member 60 is not only operable to act as a single dose limiting member but may also provide a last dose limiting mechanism. In FIG. 16a a configuration of the drive mechanism 3 is shown, where a proximal end of the piston rod 70 has already left the sleeve of the clutch 40. In this configuration, there might be only 50 I.U. of medicament left in the cartridge 14. For security reasons, the drive mechanism 3 must not set a dose exceeding this residual amount of medicament.

Figure 16B:
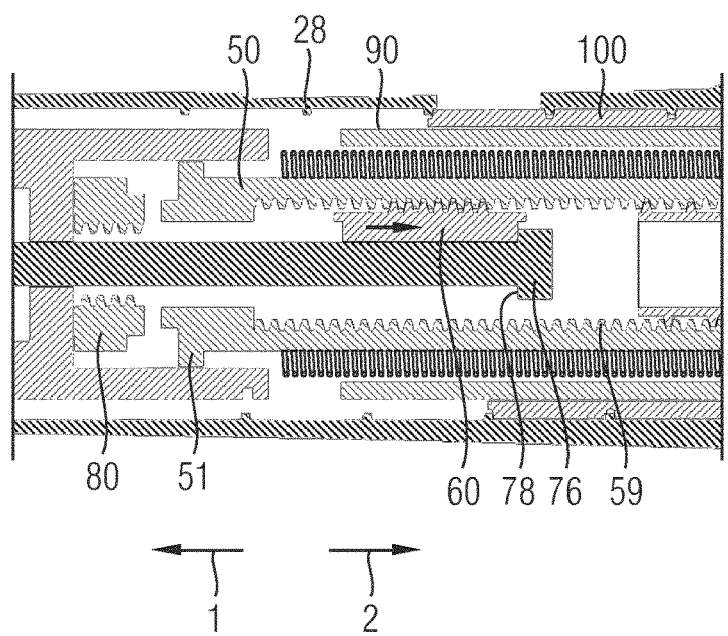

However, dose setting may take place as usual and as described above by rotating the actuation member 30 in a dose incrementing direction. This rotation leads to a corresponding rotation of the drive sleeve 50 and hence to a distally directed displacement of the dose limiting member 60 in proximal direction 2. As shown in FIGS. 16a and 16b, the dose limiting member 60 slides with a radially inwardly extending gliding portion 61 in a groove 72 of the piston rod 70. Said groove is terminated by a radially extending portion 76 at the proximal end 73 of the piston rod 70.

Hence, the groove 72 is delimited in proximal direction 2 by a last dose stop 78 extending in radial direction. During a dose setting procedure, the drive sleeve 50 is only allowed to rotate relative to piston rod 70 until the axial stop position of the dose limiting member 60 with regard to the piston rod 70 has been reached. Since the dose limiting member 60 as illustrated in FIG. 16b is hindered from sliding further in proximal direction 2 along the piston rod 70, a further dose incrementing rotation of the drive sleeve 50 is effectively blocked due to the threaded engagement of the dose limiting member 60 and the drive sleeve 50. Consequently, the dose limiting member effectively provides a last dose limiting mechanism effectively preventing that the drive mechanism 3 is set to a dose exceeding the amount of medicament contained in the cartridge 14.

The last dose limiting functionality of the dose limiting member 60 may be implemented only optionally or alternatively to the last dose limiting mechanism provided by the last dose sleeve 110 as will be explained below. Also, implementation of the last dose sleeve 110 may be optional to the last dose limiting functionality provided by the interaction of the dose limiting member 60, the piston rod 70 and the drive sleeve 50.

Figure 17A:
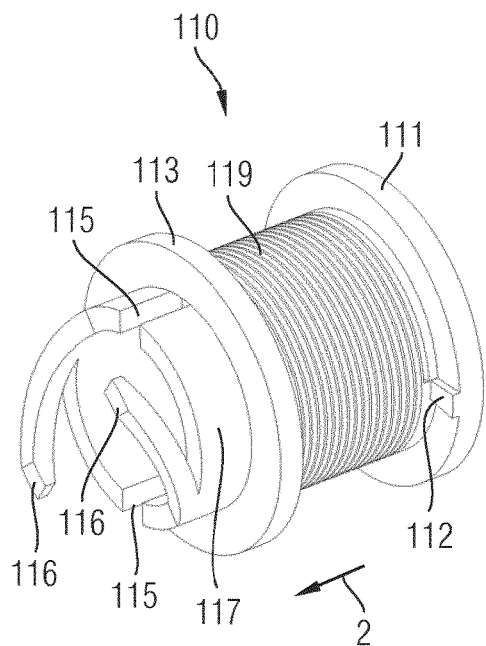
FIG. 17b shows the last dose sleeve with a last dose member assembled thereon.
Figure 17B:
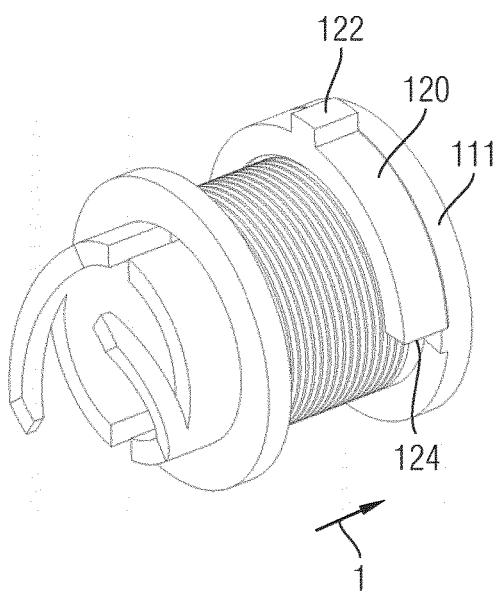
Figure 18A:
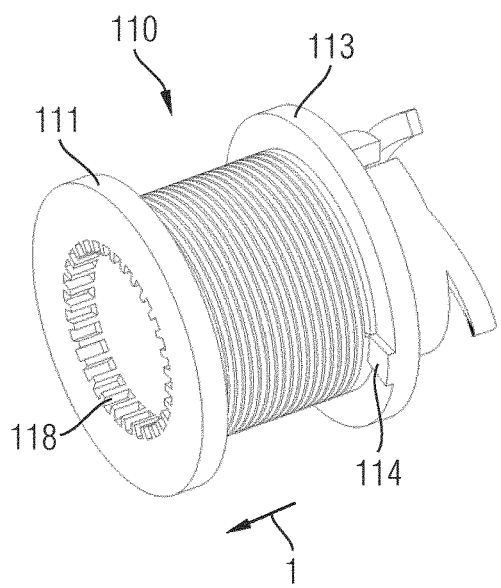
FIG. 18a shows an opposite perspective view of the last dose sleeve according to FIG. 17a and FIG. 18b shows a corresponding alternative perspective view of the last dose sleeve with the last dose member assembled thereon, FIG. 19 perspectively illustrates in a partially transparent view of the interaction of the dose limiting member and the drive sleeve during dose setting, FIG. 19a schematically shows an enlarged view of a framed section of FIG. 19, FIG. 20 schematically illustrates mutual interaction of the dose limiting member and the drive sleeve during dose dispensing
Figure 18B:
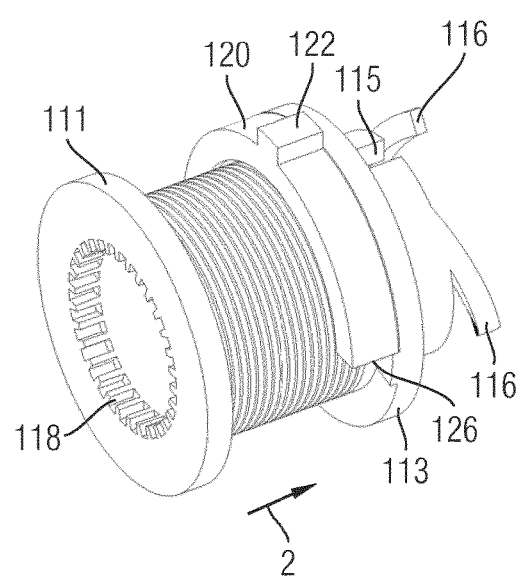

The last dose sleeve 110 as illustrated in FIGS. 8a through 8b and in FIGS. 17a to 18b comprises an outer thread 119 extending between a distal flange 111 and a proximal flange 113. The last dose sleeve 110 is further engaged, in particular threadedly engaged with a last dose member 120, which is of annular or arc-shape as illustrated in FIGS. 17b and 18b. The last dose member 120 comprises an internal thread 128 to threadedly engage with the outer thread 119 of the last dose sleeve 110 and further comprises a radially outwardly extending protrusion 122 engaged with an axially extending groove 27 provided on the inside facing sidewall of the proximal receptacle 23 of the housing 20.

The groove 27 is also illustrated in the cross section A-A in FIGS. 5a and 5b. Since the protrusion 122 of the last dose member 120 engages with the groove 27 of the housing 20, the last dose member is rotatably locked to the housing 20 and is therefore hindered to rotate with respect to the housing 20 in circumferential direction. Due to its threaded engagement with the outer thread 119 of the last dose sleeve 110, the last dose member is displaced in axial direction 1 when the last dose sleeve 110 is rotated with respect to the housing 20.

Typically, the last dose member 120 comprises a leading edge 124 and a trailing edge 126 in circumferential direction with respect to the sense of rotation of the last dose sleeve 110 relative to the last dose member 120. By means of its leading and/or trailing edges 124, 126, the last dose member 120 is engageable with the radially extending or radially protruding stop 112 or 114 provided on the outer circumference of the last dose sleeve 110 when reaching a last dose limiting configuration.

When the leading or trailing edge 124, 126 of the last dose member 120 abuts or engages with the at least one stop 112, 114 of the last dose sleeve 110, further rotation of the last dose sleeve 110 can be effectively blocked and inhibited, thereby blocking or inhibiting a further dose incrementing rotation of the actuation member 30 during a dose setting procedure. The radially and preferably also axially extending leading edge 124, 126 of the last dose member 120 and the correspondingly shaped stop 112, 114 of the last dose sleeve 110 are adapted to immediately block a further rotation of the last dose sleeve 110 and hence of the actuation member 30 when a predetermined rotational position of the last dose sleeve 110 and the actuation member 30 has been reached.

The thread 119 and the axial dimensions of the last dose sleeve 110 are selected such, that an axial position of the last dose member 120 on the last dose sleeve 110 is directly correlated to the axial position of the piston rod 70 and hence to the axial position of the piston 16 in the cartridge 14.

The last dose sleeve 110 further comprises a distal stop 112 extending radially outwardly from the distal end of the thread 119 as illustrated in FIG. 17a. As soon as a leading edge 124 of the last dose member 120 abuts with the distal stop 112 of the last dose sleeve 110 a further rotation of the last dose sleeve 110 with respect to the housing 20 and be effectively blocked. In this way, setting of a dose exceeding the filling level or the amount of medicament contained in the cartridge 12 can be effectively prevented.

The last dose sleeve 110 also comprises a proximal stop 114 as indicated in FIG. 18a. The proximal stop 114 provides a well-defined position for the last dose member 120 in an initial device configuration and for assembly of the drug delivery device and its drive mechanism 3. Here, the radially extending flange portions 111, 113 of the last dose sleeve 110 also provide a support structure for the distal stop 114 and for the proximal stop 112 both extending in radial direction from the external thread 119 of the dose sleeve 110.

It is to be mentioned here, that the last dose limiting mechanism implemented by the last dose sleeve 110 is beneficial in that the last dose sleeve 110 is directly located inside the actuation member 30. In effect, a tolerance chain between the actuation member 30 and the last dose limiting mechanism is fairly short and can therefore be reduced to a minimum.

Moreover, the flexibility of the various parts, of which the drive mechanism 3 is assembled may play a subordinate role, as the flux of force from the actuation member 30 to the last dose sleeve 110 is comparatively short. Moreover, also from a user's point of view, the position of the last dose sleeve 110 together with the last dose member 120 inside the actuation member 30 will provide a rather solid, robust and therefore very reliable last dose limiting mechanism.

LIST OF REFERENCE NUMERALS 1 distal direction
2 proximal direction
3 drive mechanism
10 drug delivery device
12 cartridge holder
14 cartridge
16 piston
17 protective cap 18 needle assembly
19 inner needle cap
20 housing
21 spring element
22 rim
23 receptacle
24 socket
25 window
26 toothed ring
27 groove
28 inner thread
30 actuation member
32 flange portion
33 journal
34 protrusion
40 clutch
42 stop
44 rib
45 tooth
46 snap portion
48 rim
49 flange
50 drive sleeve
51 ratchet member
52 groove
53 tooth
54 recess
55 recess
56 stop
56a recess
57 distal face
58 helical spring
59 internal thread
60 dose limiting member
61 gliding portion
62a distal stop portion
62b proximal stop portion
63 external thread
64 clicking member
65 proximal end face
66 latch portion
67 distal end face
68 arm
70 piston rod
71 pressure foot
72 groove
73 proximal end
74 thread
76 radially extending portion
78 stop
80 drive nut
82 proximal face
84 thread
86 ratchet member
87 tooth
90 intermediate sleeve
92 protrusion
94 recess
100 dose indicating sleeve
102 protrusion
104 dose indicating number
105 toothed surface
106 insert
107 protrusion
108 toothed surface
109 recess
110 last dose sleeve
111 distal flange
112 distal stop
113 proximal flange
114 proximal stop
115 recess
116 spring element
117 rim
118 toothed surface
119 thread
120 last dose member
122 protrusion
124 leading edge
126 trailing edge
128 internal thread

The invention claimed is:

1. A drug delivery device for dispensing of a dose of a medicament, comprising:
an elongate housing;
a cartridge arranged in the housing and comprising a piston, the cartridge being at least partially filled with the medicament;
a piston rod configured to engage the piston of the cartridge to displace the piston in a distal direction along a longitudinal axis of the housing;
a drive sleeve rotatably supported in the housing and being releasable from the piston rod for setting a dose during dose setting, the drive sleeve being engageable with the piston rod for dispensing the dose during dose dispensing;
a dose limiting member directly engaged with the drive sleeve and directly engaged with the piston rod, the dose limiting member being configured to move along the longitudinal axis relative to the drive sleeve when the drive sleeve is rotated relative to the piston rod during the dose setting; and
a stop configured to abut the dose limiting member and limit displacement of the dose limiting member during the dose setting and to inhibit rotation of the drive sleeve relative to the piston rod during the dose setting.

2. The drug delivery device of claim 1, wherein the stop is part of a clutch configured to engage with the drive sleeve, and the stop is arranged on and axially protruding from a distal end of the clutch.

3. The drug delivery device of claim 1, further comprising a helical spring extending around the drive sleeve, the spring being configured to rotatably bias the drive sleeve relative to the housing.

4. The drug delivery device of claim 1, further comprising a drive nut axially fixed to the housing and rotatably supported in the housing, the drive nut being threadedly engaged with the piston rod, wherein the drive sleeve is axially displaceable relative to the housing to rotatably engage with the drive nut during the dose dispensing and to rotatably disengage the drive sleeve from the drive nut during the dose setting.

5. The drug delivery device of claim 1, wherein the stop extends radially relative to the longitudinal axis and extends along the longitudinal axis, the stop being configured to engage with a stop portion of the dose limiting member, the stop portion extending radially relative to the longitudinal axis and extending along the longitudinal axis.

6. The drug delivery device of claim 5, wherein the dose limiting member comprises a clicking member having a resilient arm extending in a circumferential direction from the dose limiting member, the resilient arm comprising a latch portion at a free end of the resilient arm, the latch portion being configured to engage with the stop before or when the stop portion engages with the stop to generate an audible feedback.

7. A drive mechanism of a drug delivery device for dispensing of a dose of a medicament, the mechanism comprising:
- an elongated housing extending in an axial direction,
- a piston rod to operably engage with a piston of a cartridge to displace the piston in an axial distal direction,
- a drive sleeve rotatably supported in the housing and being releasable from the piston rod for setting of a dose during dose setting and being engageable with the piston rod for dispensing of the dose during dose dispensing,
- a dose limiting member directly engaged with the drive sleeve and directly engaged with the piston rod, and being configured to move along a longitudinal axis of the housing relative to the drive sleeve when the drive sleeve is rotated relative to the piston rod during the dose setting, and
- at least one stop to engage with the dose limiting member for limiting longitudinal displacement of the dose limiting member during the dose setting and to inhibit rotation of the drive sleeve relative to the piston rod during the dose setting.

8. The drive mechanism of claim 7, wherein:
the drive sleeve encloses a circumference of the piston rod at least in an axial section, and
the dose limiting member is arranged radially between the drive sleeve and the piston rod.

9. The drive mechanism of claim 7, wherein the dose limiting member is threadedly engaged with the drive sleeve.

10. The drive mechanism of claim 7, wherein the dose limiting member is rotatably fixed to the piston rod and axially slidably engaged with the piston rod.

11. The drive mechanism of claim 7, wherein a radially inwardly extending gliding portion of the dose limiting member is configured to be received by an elongated groove of the piston rod.

12. The drive mechanism of claim 7, wherein the dose limiting member is shaped to extend only partially around a circumference of the piston rod.

13. The drive mechanism of claim 7, wherein the stop extends radially relative to the longitudinal axis and extends along the longitudinal axis, the stop being configured to engage with a stop portion of the dose limiting member, the stop portion extending radially relative to the longitudinal axis and extending along the longitudinal axis.

14. The drive mechanism of claim 13, wherein the dose limiting member comprises a clicking member having a resilient arm extending in a circumferential direction from the dose limiting member, the resilient arm comprising a latch portion at a free end of the resilient arm, the latch portion being configured to engage with the stop before or when the stop portion engages with the stop to generate an audible feedback.

15. The drive mechanism of claim 7, wherein the dose limiting member comprises:
- a distal stop portion extending from a distal end section of the dose limiting member and
- a proximal stop portion extending from a proximal end section of the dose limiting member, the proximal end section being opposite the distal end section.

16. The drive mechanism of claim 7, wherein the stop is positioned on an inner wall of the drive sleeve.

17. The drive mechanism of claim 7, wherein the stop is arranged on and axially protrudes from a proximal end of a clutch configured to be engaged with the drive sleeve.

18. The drive mechanism of claim 7, wherein the stop extends radially in or on the piston rod, the stop being configured to engage with the dose limiting member in a last dose configuration to inhibit setting of an excess dose exceeding an amount of liquid remaining in a cartridge loaded in the housing.

19. The drive mechanism of claim 7, wherein the drive sleeve is rotatably biased by a helical spring extending around the drive sleeve.

20. The drive mechanism of claim 7, further comprising a drive nut axially fixed to the housing and rotatably supported in the housing, the drive nut being threadedly engaged with the piston rod,
wherein the drive sleeve is axially displaceable relative to the housing to rotatably engage with the drive nut during the dose dispensing and to rotatably disengage the drive sleeve from the drive nut during the dose setting.

21. A drive mechanism of a drug delivery device for dispensing of a dose of a medicament, the mechanism comprising:
- an elongated housing extending in an axial direction,
- a piston rod to operably engage with a piston of a cartridge to displace the piston in an axial distal direction,
- a drive sleeve rotatably supported in the housing and being releasable from the piston rod for setting of a dose during dose setting and being engageable with the piston rod for dispensing of the dose during dose dispensing,
- a dose limiting member engaged with the drive sleeve and engaged with the piston rod, and being configured to move along a longitudinal axis of the housing relative to the drive sleeve when the drive sleeve is rotated relative to the piston rod during the dose setting, and
- at least one stop to engage with the dose limiting member for limiting longitudinal displacement of the dose limiting member during the dose setting and to inhibit rotation of the drive sleeve relative to the piston rod during the dose setting, wherein the dose limiting member is rotatably fixed to the piston rod and axially slidably engaged with the piston rod.

22. A drive mechanism of a drug delivery device for dispensing of a dose of a medicament, the mechanism comprising:
- an elongated housing extending in an axial direction,
- a piston rod to operably engage with a piston of a cartridge to displace the piston in an axial distal direction,
- a drive sleeve rotatably supported in the housing and being releasable from the piston rod for setting of a dose during dose setting and being engageable with the piston rod for dispensing of the dose during dose dispensing, wherein the drive sleeve is rotatable relative to the piston rod during dose dispensing,
- a dose limiting member engaged with the drive sleeve and engaged with the piston rod, and being configured to move along a longitudinal axis of the housing relative to the drive sleeve when the drive sleeve is rotated relative to the piston rod during the dose setting, and
- at least one stop to engage with the dose limiting member for limiting longitudinal displacement of the dose limiting member during the dose setting and to inhibit rotation of the drive sleeve relative to the piston rod during the dose setting.

* * * * *